(12) United States Patent
McAfee et al.

(10) Patent No.: US 10,799,356 B2
(45) Date of Patent: Oct. 13, 2020

(54) PERCUTANEOUS PAPILLARY MUSCLE RELOCATION

(71) Applicant: BOSTON SCIENTIFIC SCIMED, INC., Maple Grove, MN (US)

(72) Inventors: Patricia McAfee, Galway (IE); Aiden Flanagan, Galway (IE); Tim O'Connor, Galway (IE); Jan Weber, Maastricht (NL); Omar Jarral, London (GB)

(73) Assignee: Boston Scientific Scimed, Inc., Maple Grove, MN (US)

( * ) Notice: Subject to any disclaimer, the term of this patent is extended or adjusted under 35 U.S.C. 154(b) by 114 days.

(21) Appl. No.: 16/116,307

(22) Filed: Aug. 29, 2018

(65) Prior Publication Data
US 2019/0076248 A1 Mar. 14, 2019

Related U.S. Application Data

(60) Provisional application No. 62/557,462, filed on Sep. 12, 2017.

(51) Int. Cl.
*A61F 2/24* (2006.01)
*A61B 17/00* (2006.01)

(52) U.S. Cl.
CPC .......... *A61F 2/2454* (2013.01); *A61F 2/2445* (2013.01); *A61F 2/2457* (2013.01);
(Continued)

(58) Field of Classification Search
CPC ........ A61F 2/24; A61F 2/2412; A61F 2/2418; A61F 2/254
(Continued)

(56) References Cited

U.S. PATENT DOCUMENTS 6,332,893 B1 12/2001 Mortier et al.
6,629,534 B1 10/2003 St. Goar et al.
(Continued)

FOREIGN PATENT DOCUMENTS

| WO | 9930647 A1 | 6/1999 |
| WO | 2007100408 A2 | 9/2007 |
| WO | 2009140298 A2 | 11/2009 |

OTHER PUBLICATIONS

Mihos et al., "Combined Papillary Muscle Sling and Ring Annuloplasty for Moderate-to-severe Secondary Mitral Regurgitation," Journal of Cardiac Surgery, 8 pages, 2016.
(Continued)

*Primary Examiner* — Suzette J Gherbi
(74) *Attorney, Agent, or Firm* — Seager, Tufte & Wickhem LLP

(57) ABSTRACT

A mitral regurgitation treatment system may include an annuloplasty device configured for placement on an atrial side of a mitral valve, a tethering element configured to extend between a first papillary muscle and a second papillary muscle, wherein the tethering element includes a first anchor securing the tethering element to the first papillary muscle and a second anchor securing the tethering element to the second papillary muscle, and a linking element extending from the annuloplasty device to the tethering element. The linking element may include a spring element disposed between the annuloplasty device and the tethering element.

19 Claims, 15 Drawing Sheets

(52) U.S. Cl.
CPC ............... *A61B 2017/00243* (2013.01); *A61F 2210/009* (2013.01)

(58) Field of Classification Search
USPC .............................................. 623/2.36–2.37
See application file for complete search history.

(56) References Cited

U.S. PATENT DOCUMENTS

| | | | |
|---|---|---|---|
| 6,797,002 | B2 | 9/2004 | Spence et al. |
| 7,608,091 | B2 | 10/2009 | Goldfarb et al. |
| 7,678,145 | B2 | 3/2010 | Vidlund et al. |
| 7,704,269 | B2 | 4/2010 | St. Goar et al. |
| 7,753,923 | B2 | 7/2010 | St. Goar et al. |
| 7,998,151 | B2 | 8/2011 | St. Goar et al. |
| 8,070,805 | B2 | 12/2011 | Vidlund et al. |
| 8,133,168 | B2 | 3/2012 | Monnet et al. |
| 8,187,299 | B2 | 5/2012 | Goldfarb et al. |
| 8,206,439 | B2 | 6/2012 | Gomez Duran |
| 8,323,334 | B2 | 12/2012 | Deem et al. |
| 8,579,967 | B2 | 11/2013 | Webler et al. |
| 8,734,505 | B2 | 5/2014 | Goldfarb et al. |
| 8,784,483 | B2 | 7/2014 | Navia |
| 9,125,742 | B2 * | 9/2015 | Yoganathan .......... A61F 2/2445 |
| 9,265,608 | B2 | 2/2016 | Miller et al. |
| 9,486,315 | B2 | 11/2016 | Chawla |
| 9,636,224 | B2 | 5/2017 | Zipory et al. |
| 10,010,419 | B2 * | 7/2018 | Yoganathan .......... A61F 2/2457 |
| 2002/0029080 | A1 * | 3/2002 | Mortier ................. A61F 2/2454 623/2.36 |
| 2004/0003819 | A1 | 1/2004 | St. Goar et al. |
| 2004/0030382 | A1 | 2/2004 | St. Goar et al. |
| 2004/0039442 | A1 | 2/2004 | St. Goar et al. |
| 2004/0148020 | A1 | 7/2004 | Vidlund et al. |
| 2005/0021056 | A1 | 1/2005 | St. Goar et al. |
| 2005/0021057 | A1 | 1/2005 | St. Goar et al. |
| 2005/0033446 | A1 | 2/2005 | Deem et al. |
| 2006/0195012 | A1 | 8/2006 | Mortier et al. |
| 2006/0241340 | A1 | 10/2006 | Schroeder et al. |
| 2006/0281968 | A1 | 12/2006 | Duran et al. |
| 2007/0038293 | A1 | 2/2007 | St. Goar et al. |
| 2008/0051807 | A1 | 2/2008 | St. Goar et al. |
| 2008/0167714 | A1 | 7/2008 | St. Goar et al. |
| 2008/0228272 | A1 | 9/2008 | Moaddeb et al. |
| 2009/0082619 | A1 | 3/2009 | De Marchena |
| 2009/0099410 | A1 * | 4/2009 | De Marchena .. A61B 17/00234 600/37 |
| 2009/0198322 | A1 | 8/2009 | Deem et al. |
| 2009/0287037 | A1 | 11/2009 | Monnet et al. |
| 2009/0292353 | A1 * | 11/2009 | Yoganathan ..... A61B 17/00234 623/2.11 |
| 2010/0016958 | A1 | 1/2010 | St. Goar et al. |
| 2010/0023117 | A1 * | 1/2010 | Yoganathan .......... A61F 2/2445 623/2.11 |
| 2010/0185276 | A1 | 7/2010 | Vidlund et al. |
| 2010/0217283 | A1 | 8/2010 | St. Goar et al. |
| 2011/0015476 | A1 | 1/2011 | Franco |
| 2011/0230961 | A1 * | 9/2011 | Langer ................. A61F 2/2448 623/2.27 |
| 2011/0230962 | A1 | 9/2011 | Moaddeb et al. |
| 2011/0264208 | A1 | 10/2011 | Duffy et al. |
| 2012/0197388 | A1 | 8/2012 | Hairkhahan et al. |
| 2013/0282059 | A1 | 10/2013 | Ketai et al. |
| 2014/0142689 | A1 | 5/2014 | De Canniere et al. |
| 2015/0351909 | A1 * | 12/2015 | Bobo, Jr. ............... A61F 2/2445 623/2.37 |
| 2015/0374494 | A1 | 12/2015 | Yoganathan et al. |
| 2016/0302917 | A1 * | 10/2016 | Schewel ............... A61F 2/2412 |
| 2017/0119368 | A1 | 5/2017 | Solem |
| 2017/0172741 | A1 | 6/2017 | Subramanian et al. |
| 2017/0224487 | A1 * | 8/2017 | Konno .................. A61F 2/2412 |
| 2017/0245994 | A1 * | 8/2017 | Khairkhahan .......... A61L 27/06 |
| 2017/0252153 | A1 * | 9/2017 | Chau ..................... A61F 2/2418 |
| 2019/0076248 | A1 * | 3/2019 | McAfee ............... A61F 2/2457 |
| 2019/0083264 | A1 * | 3/2019 | Jarral ................. A61B 17/0401 |
| 2019/0358037 | A1 * | 11/2019 | McAfee ................ A61B 17/30 |
| 2020/0038179 | A1 * | 2/2020 | Vidlund ............. A61L 27/3629 |

OTHER PUBLICATIONS

Glower, "Surgical Approaches to Mitral Regurgitation," Journal of the American College of Cardiology, vol. (60): 8 pages, 2012.
International Search Report and Written Opinion dated Nov. 26, 2018 for International Application No. PCT/US2018/048533.

* cited by examiner

PERCUTANEOUS PAPILLARY MUSCLE RELOCATION

CROSS-REFERENCE TO RELATED APPLICATIONS

This application claims the benefit of priority under 35 U.S.C. § 119 to U.S. Provisional Application Ser. No. 62/557,462, filed Sep. 12, 2017, the entirety of which is incorporated herein by reference.

TECHNICAL FIELD

The present disclosure pertains to medical devices and methods for using medical devices. More particularly, the present disclosure pertains to aspects of medical devices and/or means to deliver and release medical devices for percutaneously treating mitral regurgitation by relocating the papillary muscles of the heart.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, occlusive medical devices, etc.), and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, a mitral regurgitation treatment system may comprise an annuloplasty device configured for placement on an atrial side of a mitral valve; a tethering element configured to extend between a first papillary muscle and a second papillary muscle, wherein the tethering element includes a first anchor securing the tethering element to the first papillary muscle and a second anchor securing the tethering element to the second papillary muscle; and a linking element extending from the annuloplasty device to the tethering element. The linking element may include a spring element disposed between the annuloplasty device and the tethering element.

In addition or alternatively, and in a second aspect, the linking element connects to the tethering element along a length of the tethering element.

In addition or alternatively, and in a third aspect, the linking element is configured to connect to the tethering element at a location between the first papillary muscle and the second papillary muscle.

In addition or alternatively, and in a fourth aspect, the spring element maintains the linking element in tension between the annuloplasty device and the tethering element.

In addition or alternatively, and in a fifth aspect, the mitral regurgitation treatment system may further comprise a crimping element disposed on the linking element and configured to engage an outer surface of the annuloplasty device.

In addition or alternatively, and in a sixth aspect, the linking element extends through the annuloplasty device.

In addition or alternatively, and in a seventh aspect, the linking element extends through the annuloplasty device in a direction generally parallel to fluid flow through the mitral valve.

In addition or alternatively, and in an eighth aspect, the linking element is configured to extend through tissue of the mitral valve.

In addition or alternatively, and in a ninth aspect, the spring element is formed from nitinol.

In addition or alternatively, and in a tenth aspect, a mitral regurgitation treatment system may comprise an annuloplasty device configured for placement on an atrial side of a mitral valve; a tethering element configured to extend between a first papillary muscle and a second papillary muscle, wherein the tethering element includes a first anchor securing the tethering element to the first papillary muscle and a second anchor securing the tethering element to the second papillary muscle; and a linking element extending from the annuloplasty device to the tethering element. The first anchor may include a first anchoring element configured to be positioned against an outer surface of the first papillary muscle and a second anchoring element configured to be positioned against the outer surface of the first papillary muscle opposite the first anchoring element such that the first papillary muscle is disposed between the first anchoring element and the second anchoring element and a first portion of the tethering element passes through the first papillary muscle.

In addition or alternatively, and in an eleventh aspect, the second anchor includes a third anchoring element configured to be positioned against an outer surface of the second papillary muscle and a fourth anchoring element configured to be positioned against the outer surface of the second papillary muscle opposite the third anchoring element such that the second papillary muscle is disposed between the third anchoring element and the fourth anchoring element and a second portion of the tethering element passes through the second papillary muscle.

In addition or alternatively, and in a twelfth aspect, the linking element is connected to the tethering element between the first portion and the second portion.

In addition or alternatively, and in a thirteenth aspect, the linking element is slidable along the tethering element.

In addition or alternatively, and in a fourteenth aspect, at least one of the tethering element and the linking element comprise a multi-strand suture.

In addition or alternatively, and in a fifteenth aspect, the tethering element is configured to extend between the first papillary muscle and the second papillary muscle in tension.

In addition or alternatively, and in a sixteenth aspect, a method of delivering a mitral regurgitation system may comprise:

inserting a delivery catheter percutaneously through a vasculature to a left atrium of a heart;

deploying an annuloplasty device from the delivery catheter on an atrial side of a mitral valve of the heart;

extending a tethering element through the annuloplasty device and into a left ventricle of the heart;

anchoring the tethering element to a first papillary muscle;

anchoring the tethering element to a second papillary muscle such that the tethering element is in tension between the first papillary muscle and the second papillary muscle; and securing a linking element extending from the tethering element to the annuloplasty device in tension, the linking element including a spring element disposed between the annuloplasty device and the tethering element.

In addition or alternatively, and in a seventeenth aspect, extending the tethering element includes extending an anchor delivery catheter from the delivery catheter through the annuloplasty device and into the left ventricle of the heart.

In addition or alternatively, and in an eighteenth aspect, anchoring the tethering element to the first papillary muscle includes passing a first portion of the tethering element through the first papillary muscle.

In addition or alternatively, and in a nineteenth aspect, anchoring the tethering element to the second papillary muscle includes passing a second portion of the tethering element through the second papillary muscle.

In addition or alternatively, and in a twentieth aspect, securing the linking element includes feeding a crimping element over the linking element and into engagement with the annuloplasty device.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
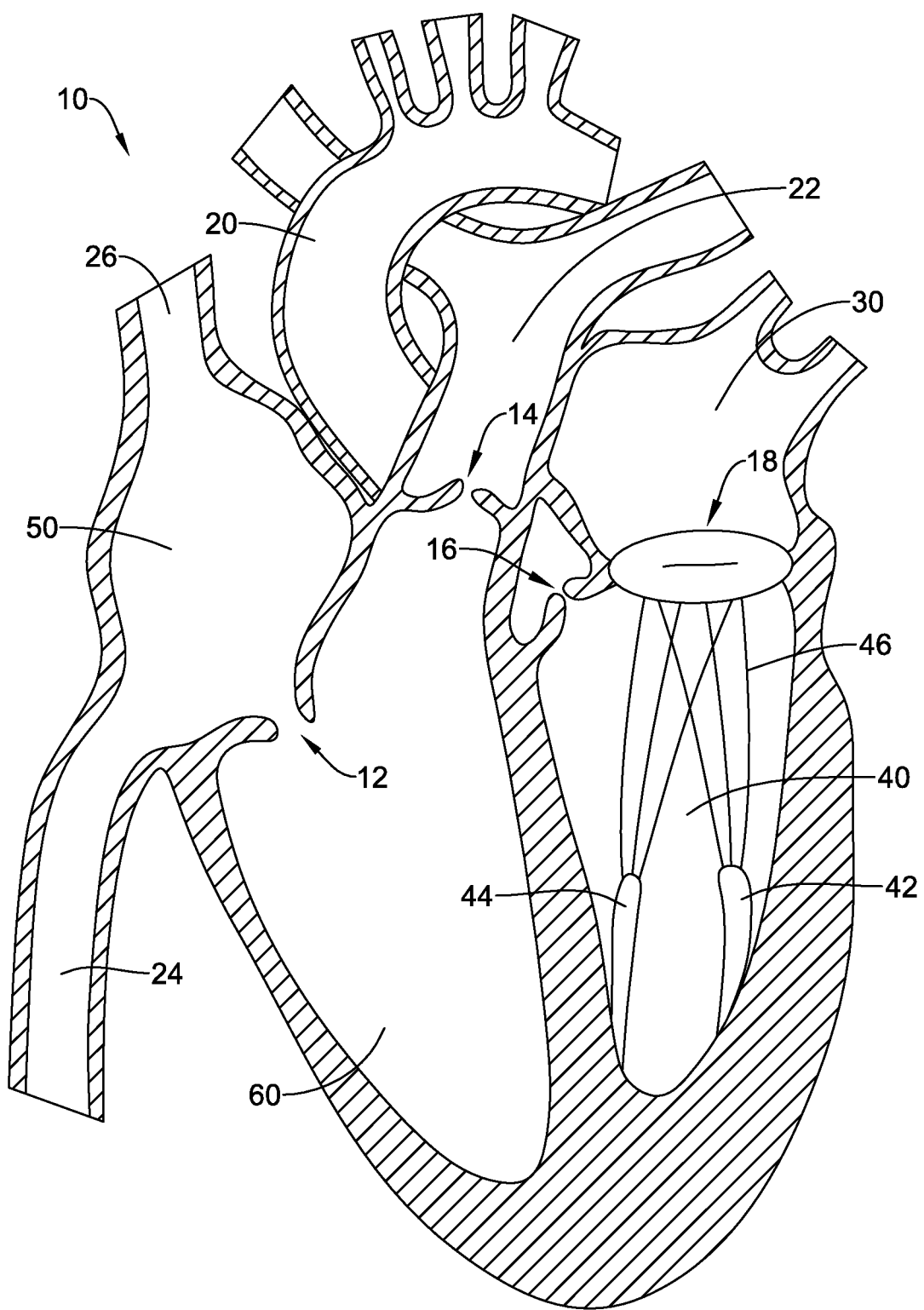
FIG. 1 is a partial cut-away view of an example heart having a "normal" left ventricle.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Some mammalian hearts (e.g., human, etc.) include four heart valves: a tricuspid valve 12, a pulmonary valve 14, an aortic valve 16, and a mitral valve 18, as seen in an example heart 10 illustrated in FIG. 1. The purpose of the heart valves is to control blood flow into the heart 10 from the inferior vena cava 24 and/or the superior vena cava 26, through the heart 10, and out of the heart 10 into the major blood vessels connected to the heart 10, such as the aorta 20, the pulmonary artery 22, for example. Each heart valve may have a plurality of valve leaflets configured to shift between an open configuration permitting fluid flow through the heart valve in an antegrade direction, and a closed configuration wherein free edges of the valve leaflets coapt to substantially prevent fluid flow through the heart valve in a retrograde direction. The heart 10 may also include a left atrium 30, a left ventricle 40, a right atrium 50, and a right ventricle 60. The left ventricle 40 may include a first papillary muscle 42 attached to and/or extending from a wall of the left ventricle 40, a second papillary muscle 44 attached to and/or extending from the wall of the left ventricle 40, and a plurality of chordae 46 connecting the first papillary muscle 42 and the second papillary muscle 44 to the leaflets of the mitral valve 18. In a normally functioning heart valve, blood is permitted to pass or flow downstream through the heart valve (e.g., from an atrium to a ventricle, from a ventricle to an artery, etc.) when the heart valve is open (e.g., during diastole), and when the heart valve is closed (e.g., during systole), blood is prevented from passing or flowing back upstream through the heart valve (e.g., from a ventricle to an atrium, etc.).

Figure 2:
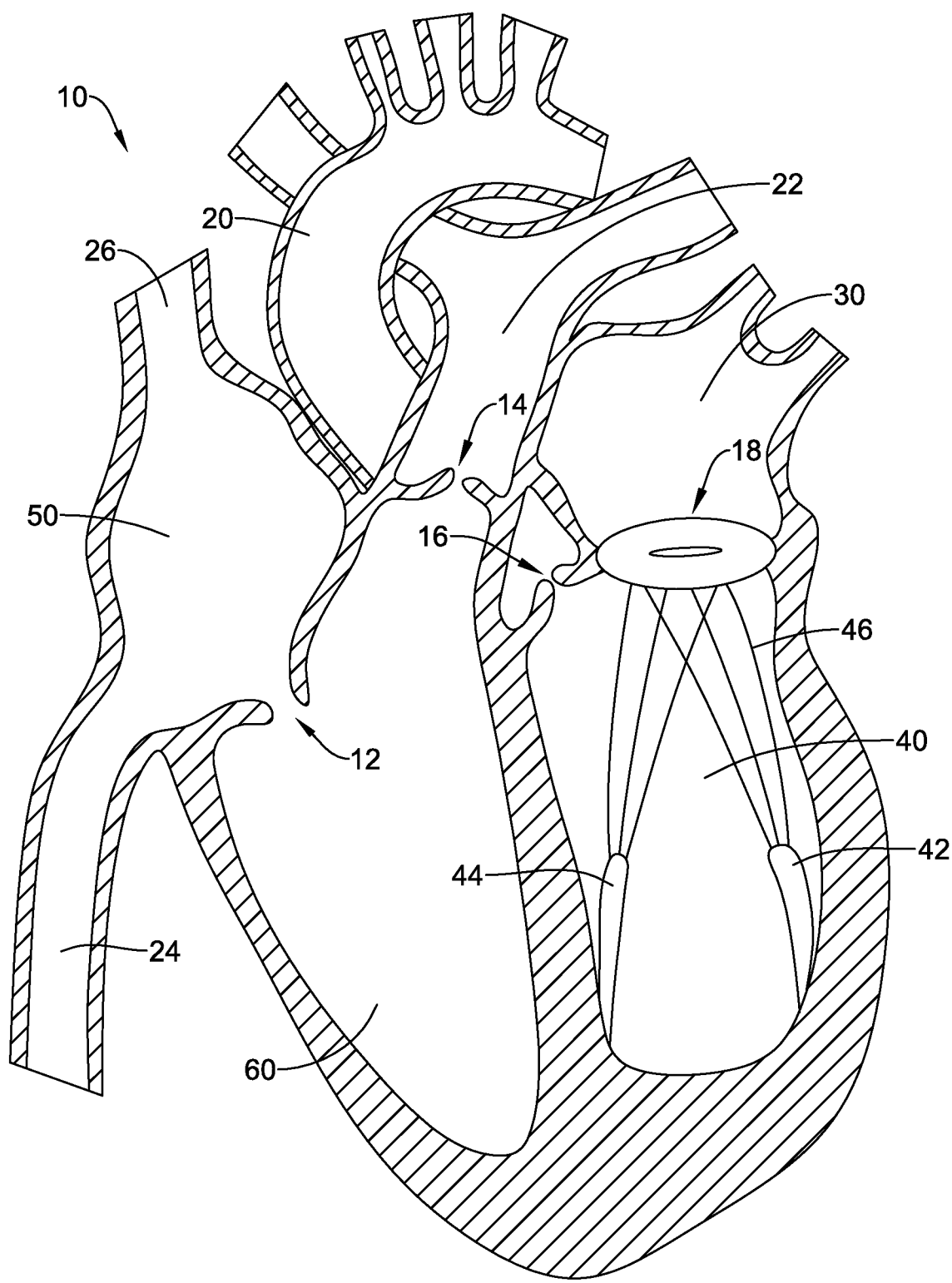
FIG. 2 is a partial cut-away view of an example heart having a "distended" left ventricle.

In some instances, when regurgitation (e.g., mitral regurgitation) occurs, a heart valve (e.g., the mitral valve 18) fails to open and/or close properly such that blood is permitted to pass or flow back upstream through the heart valve (e.g., from a ventricle to an atrium, etc.). In some cases, the defective heart valve may have leaflets that may not close, or may not be capable of closing, completely. In some instances, secondary or functional mitral regurgitation may be a secondary effect of left ventricular dysfunction, where left ventricular dilatation and/or distension caused by ischemic or idiopathic cardiomyopathy, for example, results in annular dilatation and/or distension of the left ventricle 40 and papillary muscle displacement with subsequent leaflet tethering and insufficient coaptation of the mitral leaflets during systole, as seen in FIG. 2 for example. As the left ventricle 40 dilates and/or distends outward, the first and second papillary muscles 42/44 are displaced outward and/or away from the mitral valve 18. Displacement of the first and second papillary muscles 42/44 adds tension to the chordae 46 connecting the first and second papillary muscles 42/44 to the mitral valve leaflets, and/or changes the tension to the chordae 46 with respect to a directional vector of the tension, resulting in leaflet tethering and/or insufficient coaptation of the mitral leaflets during systole.

Disclosed herein are apparatus, medical devices, and/or methods that may be used to diagnose, treat, and/or repair a portion of the cardiovascular system. One possible remedy is an annular reduction procedure that may be performed to reduce an overall extent of the defective heart valve to bring the heart valve leaflets closer together in conjunction with a sub-valvular repair technique involving relocation of the papillary muscles to reduce leaflet tethering, thereby permitting the heart valve leaflets to properly close the heart valve to the passage of blood. The disclosed mitral regurgitation treatment method(s) and associated medical device(s) may be performed/used percutaneously via minimally-invasive intravascular techniques, or in an alternative method, using open-heart surgical methods. The device(s) and method(s) disclosed herein may also provide a number of additional desirable features and/or benefits as described in more detail below. For the purpose of this disclosure, the discussion below is directed toward repairing the mitral valve 18 and will be so described in the interest of brevity. This, however, is not intended to be limiting as the skilled person will recognize that the following discussion may also apply to the aortic valve or another heart valve with no or minimal changes to the structure and/or scope of the disclosure.

Figure 3:
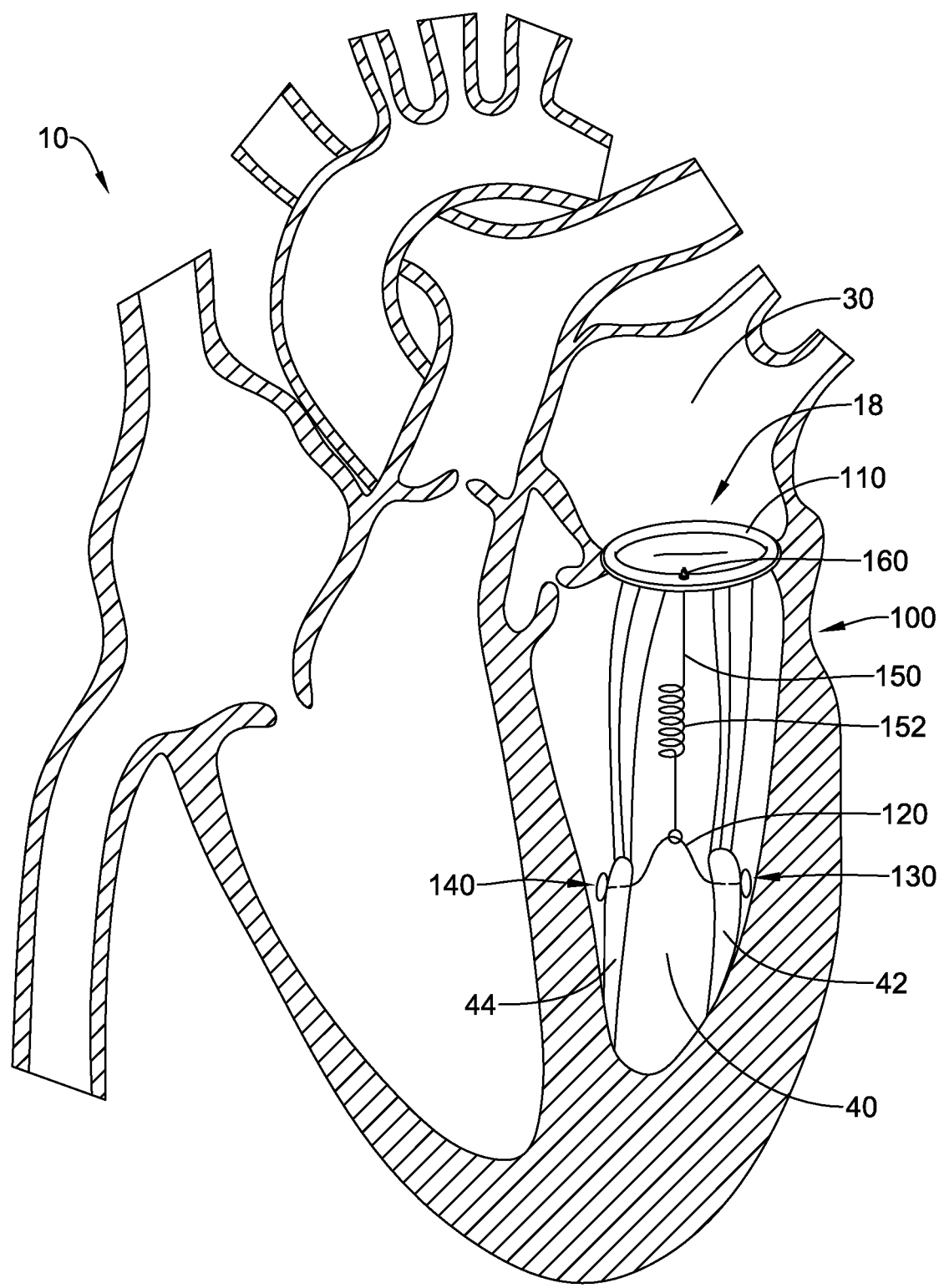
FIGS. 3-4B illustrate example configurations of a mitral regurgitation treatment system positioned relative to a mitral valve of the heart.

FIG. 3 illustrates an example mitral regurgitation treatment system 100 disposed within the heart 10 relative to the left atrium 30, the mitral valve 18, and the left ventricle 40. The mitral regurgitation treatment system 100 may reposition the first papillary muscle 42 and/or the second papillary muscle 44 relative to each other, relative to the wall of the left ventricle 40, and/or relative to the mitral valve 18 and/or the annulus of the mitral valve 18. In some embodiments, the mitral regurgitation treatment system 100 may pull the first papillary muscle 42 closer to the second papillary muscle 44. In some embodiments, pulling the first papillary muscle 42 closer to the second papillary muscle 44 may also relocate the wall of the left ventricle 40, thereby reducing and/or eliminating the magnitude of dilatation and/or distension of the left ventricle 40, which also serves to reduce tension on the chordae 46, reduce leaflet tethering, and improves coaptation of the mitral leaflets during systole. In some embodiments, pulling the first papillary muscle 42 closer to the second papillary muscle 44 may have limited effect upon the wall of the left ventricle 40 but may still reduce tension on the chordae 46, reduce leaflet tethering, and improves coaptation of the mitral leaflets during systole due to relocation of the first and second papillary muscles 42/44 closer to each other and/or the mitral valve 18.

The mitral regurgitation treatment system 100 may include an annuloplasty device 110 configured for placement on an atrial side of the mitral valve 18. In some embodiments, at least a portion of the annuloplasty device may extend to a ventricular side of the mitral valve 18. In some embodiments, the annuloplasty device 110 may comprise an annuloplasty ring configured to reduce the size of the annulus of the mitral valve 18 to bring free edges of the leaflets closer together and/or into coaptation with each other. In at least some embodiments, the annuloplasty device 110 may be positioned on and/or against the mitral valve 18 on an atrial side of the leaflets of the mitral valve 18. In some embodiments, the annuloplasty device 110 and/or the annuloplasty ring may be fixedly secured to tissue of the mitral valve 18, for example the annulus of the mitral valve 18. Some suitable but non-limiting materials for the annuloplasty device 110, and/or the annuloplasty ring, for example metallic materials, polymer materials, composite materials, etc., are described below.

The mitral regurgitation treatment system 100 may include a tethering element 120 configured to extend between the first papillary muscle 42 and the second papillary muscle 44. The tethering element 120 may include a first anchor 130 securing the tethering element 120 to the first papillary muscle 42, and a second anchor 140 securing the tethering element 120 to the second papillary muscle 44. In some embodiments, the tethering element 120 may be configured to extend between the first papillary muscle 42 and the second papillary muscle 44 in tension.

Figure 3A:
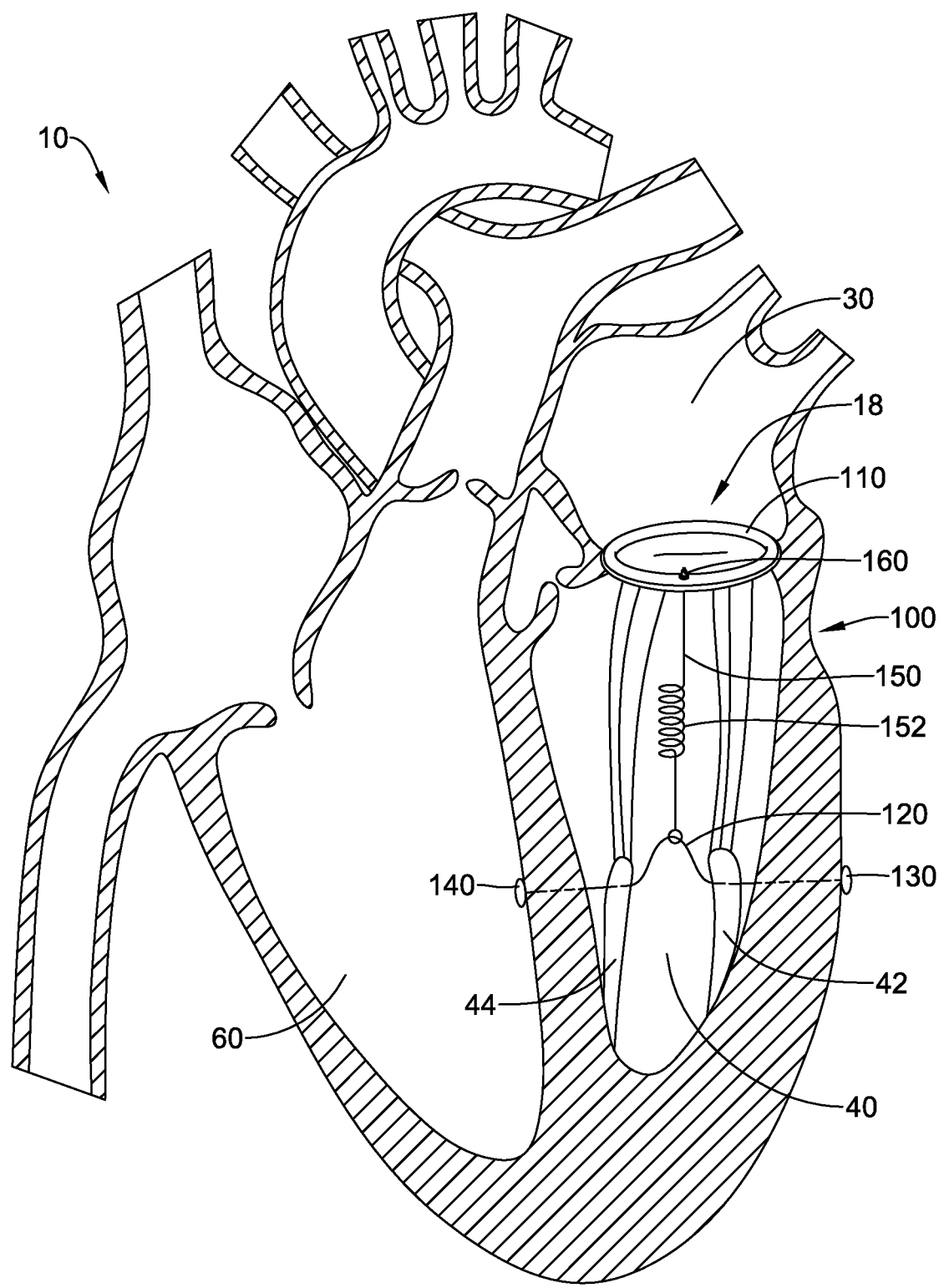

In at least some embodiments, the first anchor 130 may be configured to be positioned against an outer surface of the first papillary muscle 42. In an alternative example (e.g., FIG. 3A), the first anchor 130 may be configured to be positioned against an outer surface of a wall of the left ventricle 40 and/or an outer surface of the heart 10. In some embodiments, the first anchor 130 may comprise a pledget, a rivet, a screw-type anchor, a clip, a staple, or another suitable anchoring element. In at least some embodiments, a first end of the tethering element 120 may be fixedly secured and/or attached to the first anchor 130. In some embodiments, a first portion of the tethering element 120 may pass through the first papillary muscle 42 and/or the wall of the left ventricle 40. In at least some embodiments, the second anchor 140 may be configured to be positioned against an outer surface of the second papillary muscle 44. In the alternative example of FIG. 3A, the second anchor 140 may be configured to be positioned against an outer surface of a wall of the left ventricle 40 and/or an inner surface of a wall of the right ventricle 60. In some embodiments, the second anchor 140 may comprise a pledget, a rivet, a screw-type anchor, a clip, a staple, or another suitable anchoring element. In at least some embodiments, a second end of the tethering element 120 may be fixedly secured and/or attached to the second anchor 140. In some embodiments, a second portion of the tethering element 120 different from and/or opposite the first portion of the tethering element may pass through the second papillary muscle 44 and/or the wall between the left ventricle 40 and the right ventricle 60.

In some embodiments, the first anchor 130 and the second anchor 140 may face in opposite directions. For example, in some embodiments, the first anchor 130 and the second anchor 140 may be positioned on the outer surface of their respective papillary muscle 42/44 and/or the wall of the left ventricle 40 such that the first papillary muscle 42 and the second papillary muscle 44 are both positioned between the first anchor 130 and the second anchor 140. In some embodiments, the first anchor 130 and the second anchor 140 may face towards each other. For example, in some embodiments, the first anchor 130 and the second anchor 140 may be positioned on the outer surface of their respective papillary muscle 42/44 such that neither the first papillary muscle 42 nor the second papillary muscle 44 is positioned between the first anchor 130 and the second anchor 140. Some suitable but non-limiting materials for the tethering element 120, the first anchor 130, and/or the second anchor 140, for example metallic materials, polymer materials, composite materials, synthetic materials, etc., are described below.

The mitral regurgitation treatment system 100 may include a linking element 150 extending from the annuloplasty device 110 to the tethering element 120. In some embodiments, the linking element 150 connects to the tethering element 120 along a length of the tethering element 120. In some embodiments, the linking element 150 may be slidable along the length of the tethering element 120. In some embodiments, the linking element 150 is configured to be connected to the tethering element 120 at a location between the first portion of the tethering element 120 and the second portion of the tethering element 120. In some embodiments, the linking element 150 is configured to be connected to the tethering element 120 at a location between the first papillary muscle 42 and the second papillary muscle 44. In some embodiments, the linking element 150 is configured to be connected to the tethering element 120 at a location between the first anchor 130 and the second anchor 140.

In some embodiments, the linking element 150 extends through an anterior segment of the annuloplasty device 110. In some embodiments, the linking element 150 extends through the annuloplasty device 110 in a direction generally parallel to fluid flow through the mitral valve 18. In some embodiments, the linking element 150 is configured to extend through anterior tissue of the mitral valve 18 and/or the annulus of the mitral valve 18. For example, the annuloplasty device 110 and/or the linking element 150 may be positioned and/or oriented relative to the mitral valve 18 such that the linking element 150 extends through the annuloplasty device 110 and anterior tissue of the mitral valve 18 (e.g., annulus, leaflet, etc.) at approximately a right angle to the coapting free edges of the valve leaflets. In some embodiments, the linking element 150 may engage and/or extend through one or more portions of the annuloplasty device 110 disposed on the atrial side of the mitral valve 18, the ventricular side of the mitral valve 18, or both.

In at least some embodiments, the linking element 150 may include a spring element 152 disposed between the annuloplasty device 110 and the tethering element 120. In some embodiments, the spring element 152 may maintain the linking element 150 in tension between the annuloplasty device 110 and the tethering element 120. In some embodiments, the spring element 152 may maintain and/or assist in maintaining the tethering element 120 in tension between the first papillary muscle 42 and the second papillary muscle 44. In at least some embodiments, the spring element 152 may be formed from a resilient material and/or a shape memory material, for example nitinol. Some suitable but non-limiting materials for the linking element 150 and/or the spring element 152, for example metallic materials, polymer materials, composite materials, etc., are described below.

In an alternative configuration, the mitral regurgitation system may include a replacement heart valve implant—for example, an expandable frame having a plurality of valve leaflets disposed therein configured for implantation within a native heart valve. The linking element 150 may extend from the replacement heart valve implant to the tethering element 120 as described above with respect to the annuloplasty device 110. In some embodiments, the linking element 150 and the tethering element 120 may be implant concurrently with replacement heart valve implant. In some embodiments, the linking element 150 and the tethering element 120 may be added subsequent to implantation of the replacement heart valve implant.

In some embodiments, the mitral regurgitation treatment system 100 may include a crimping element 160 disposed on and/or over the linking element 150. The crimping element 160 may be configured to engage an outer surface of the annuloplasty device 110. In some embodiments, the crimping element 160 may be configured to be positioned in facing engagement with a superiorly-facing surface of the annuloplasty device 110 and/or a surface of the annuloplasty device 110 substantially opposite the mitral valve 18, the annulus of the mitral valve 18, and/or the valve leaflets. The crimping element 160 may be shiftable between an open configuration, wherein the crimping element 160 is freely slidable along the linking element 150, and a deformed configuration, wherein the crimping element 160 has been deformed into clamping engagement with the linking element 150 and the crimping element is fixed in place on the linking element 150 and no longer slidable along the linking element 150. After positioning the mitral regurgitation treatment system 100, the annuloplasty device 110, the tethering element 120, and/or the linking element 150 in a desired position within the heart 10 relative to the left atrium 30, the mitral valve 18, and/or the left ventricle 40, the crimping element 160 may be secured in place on the linking element 150 to cooperate with the spring element 152 and/to maintain the tethering element 120 and/or the linking element 150 in tension as desired to reposition the papillary muscles 42/44. Some suitable but non-limiting materials for the crimping element 160, for example metallic materials, polymer materials, composite materials, etc., are described below.

Figure 4:
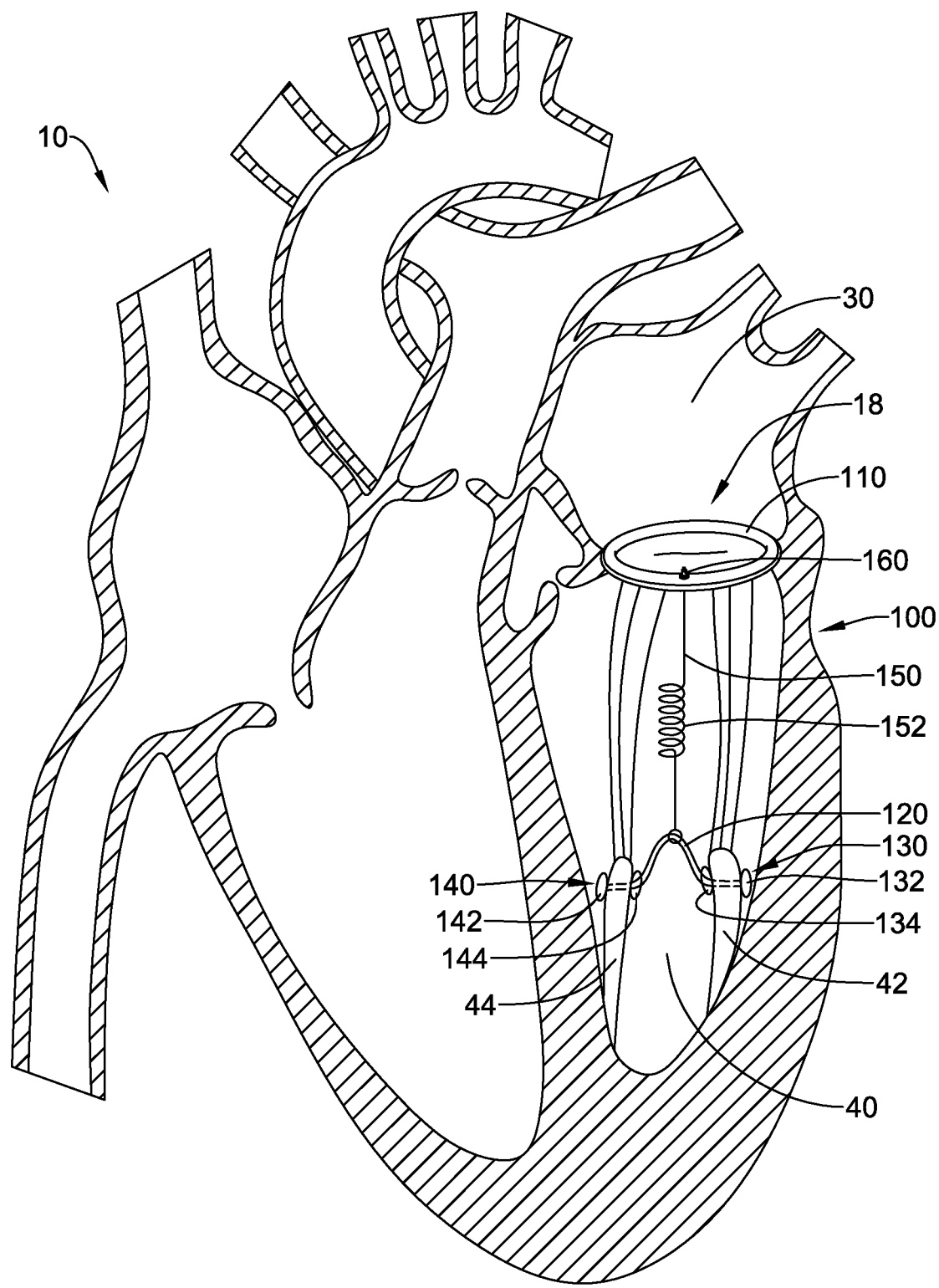

FIG. 4 illustrates an example mitral regurgitation treatment system 100 disposed within the heart 10 relative to the left atrium 30, the mitral valve 18, and the left ventricle 40. The mitral regurgitation treatment system 100 may be substantially identical to that shown in and described with respect to FIG. 3. In addition, or alternatively, in some embodiments, the first anchor 130 may include a first anchor element 132 configured to be positioned against the outer surface of the first papillary muscle 42 and a second anchor element 134 configured to be positioned against the outer surface of the first papillary muscle 42 opposite the first anchor element 132 such that the first papillary muscle 42 is disposed between the first anchor element 132 and the second anchor element 134, and the first portion of the tethering element 120 passes through the first papillary muscle 42. In at least some embodiments, the first end of the tethering element 120 may be fixedly secured and/or attached to the first anchor element 132, and/or the tethering element 120 may be fixedly secured and/or attached to the second anchor element 134. In some embodiments, the first anchor element 132 and the second anchor element 134 may face in opposite directions relative to and/or away from the first papillary muscle 42.

In some embodiments, the second anchor 140 may include a third anchor element 142 configured to be positioned against the outer surface of the second papillary muscle 44 and a fourth anchor element 144 configured to be positioned against the outer surface of the second papillary muscle 44 opposite the third anchor element 142 such that the second papillary muscle 44 is disposed between the third anchor element 142 and the fourth anchor element 144, and the second portion of the tethering element 120 passes through the second papillary muscle 44. In at least some embodiments, the second end of the tethering element 120 may be fixedly secured and/or attached to the third anchor element 142, and/or the tethering element 120 may be fixedly secured and/or attached to the fourth anchor element 144. In some embodiments, the third anchor element 142 and the fourth anchor element 144 may face in opposite directions relative to and/or away from the second papillary muscle 44. In some embodiments, some or each of the first anchor element 132, the second anchor element 134, the third anchor element 142, and/or the fourth anchor element 144 may comprise a pledget, a rivet, a screw-type anchor, a clip, a staple, or another suitable anchoring element. Some suitable but non-limiting materials for the first anchor element 132, the second anchor element 134, the third anchor element 142, and/or the fourth anchor element 144, for example metallic materials, polymer materials, composite materials, etc., are described below.

In an alternative configuration (e.g., FIG. 4A), the tethering element 120 may be fixedly secured to the second anchor element 134 and the fourth anchor element 144 at opposing ends of the tethering element 120. The first portion of the tethering element 120 may pass through the first papillary muscle 42 and the second portion of the tethering element 120 may pass through the second papillary muscle 44 in an outward direction relative to a space between the first papillary muscle 42 and the second papillary muscle 44. The tethering element 120 may then come together above the first papillary muscle 42 and the second papillary muscle 44, where the tethering element 120 is engaged by the linking element 150 as described above. As tension is applied to the linking element 150, for example by the spring element 152, the tethering element 120 may be pulled upward such that the first papillary muscle 42 and the second papillary muscle 44 are pulled toward each other, thereby reducing the space between the first papillary muscle 42 and the second papillary muscle 44.

In another alternative configuration (e.g., FIG. 4B), the tethering element 120 may be fixedly secured to the first anchor 130 and/or the first anchor element 132 while also passing therethrough to the space between the first papillary muscle 42 and the second papillary muscle 44. The first portion of the tethering element 120 passes through the first papillary muscle 42 and the second portion of the tethering element 120 passes through the second papillary muscle 44 as described above with respect to FIG. 3. The tethering element 120 is fixedly secured to the second anchor 140 and/or the third anchor element 142 at a distal end of the tethering element 120 proximate the second papillary muscle 44. The space between the first papillary muscle 42 and the second papillary muscle 44 may be reduced as desired by tightening and/or pulling on the tethering element 120 and securing the first anchor 130 and/or the first anchor element 132 at a desired position along the tethering element 120 to maintain the space between the first papillary muscle 42 and the second papillary muscle 44 at a desired amount. The tethering element 120 may extend away from the first anchor 130 and/or the first anchor element 132 and a proximal end of the tethering element 120 engages the linking element 150, which may maintain tension on the tethering element 120 and/or the first papillary muscle 42 and the second papillary muscle 44 as described herein. While not explicitly shown in FIG. 4B, the second anchor element 134 and/or the fourth anchor element 144 may also be present and/or used against the first papillary muscle 42 and the second papillary muscle 44 similar to the manner described above.

In some embodiments, the mitral regurgitation treatment system 100, the tethering element 120, and/or the linking element 150 may draw and/or relocate the first papillary muscle 42 closer to the second papillary muscle 44. In some embodiments, the mitral regurgitation treatment system 100, the tethering element 120, and/or the linking element 150 may draw and/or relocate the first papillary muscle 42 into contact with the second papillary muscle 44. For example, in some embodiments, the space between the first papillary muscle 42 and the second papillary muscle 44 may be eliminated and/or reduced to zero. This arrangement and/or configuration may be equally applied to any configuration disclosed herein.

Figure 4A:
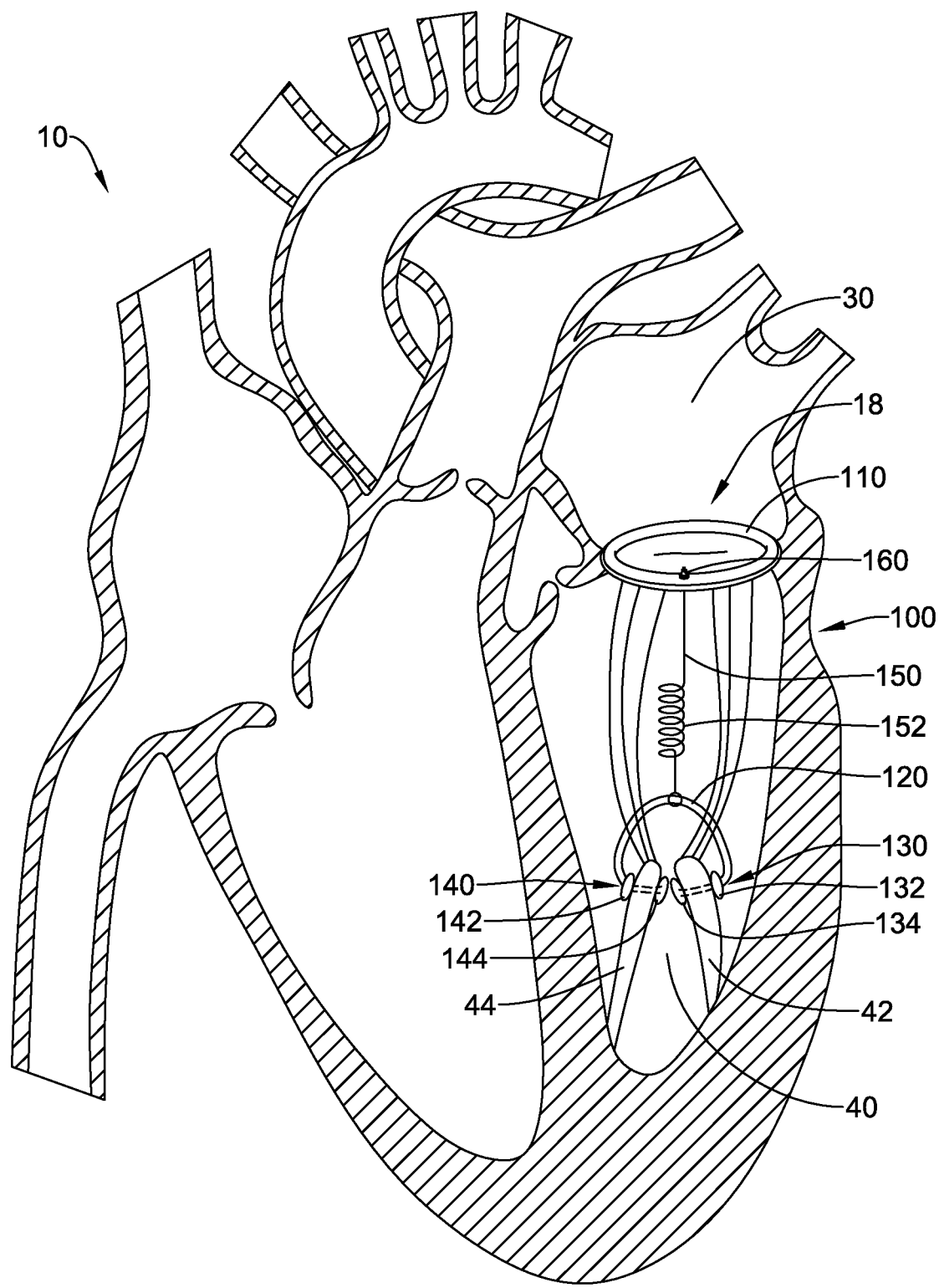
Figure 4B:
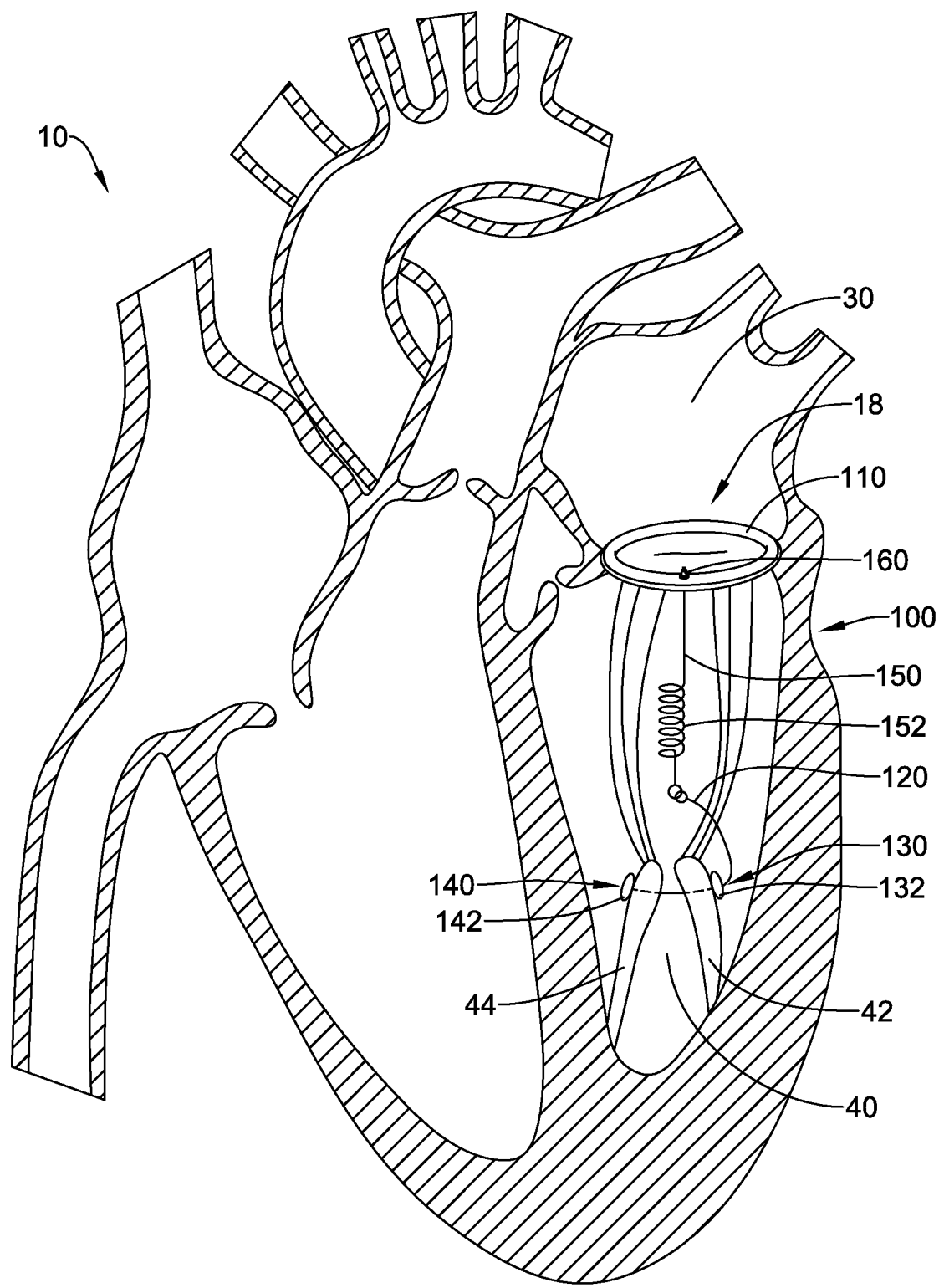

In addition or alternatively, in some embodiments, at least one of the tethering element 120 and the linking element 150 may comprise a multi-strand suture, wire, and/or filament, etc. For the purpose of illustration only, a multi-strand tethering element 120 is shown in FIGS. 4 and 4A. It is to be clearly understood that the multi-strand tethering element 120 of FIGS. 4 and 4A may be equally used in the configurations shown in FIGS. 3, 3A, and 4B (and any other configurations illustrated herein), and a multi-strand linking element 150 may be used in any configuration illustrated herein.

A multi-strand tethering element 120 may generally comprise two or more parallel strands, wires, and/or filaments, etc. configured to extend between the first papillary muscle 42 and the second papillary muscle 44. In some embodiments, the multi-strand tethering element 120 may generally comprise two or more parallel strands, wires, and/or filaments, etc. configured to extend between the first papillary muscle 42 and the second papillary muscle 44 in tension. In some embodiments, the multi-strand tethering element 120 may generally comprise two or more parallel strands, wires, and/or filaments, etc. fixedly secured and/or attached to, and/or configured to extend between the first anchor 130 and the second anchor 140 in tension. In some embodiments, the multi-strand tethering element 120 may generally comprise two or more parallel strands, wires, and/or filaments, etc. fixedly secured and/or attached to, and/or configured to extend between the first anchor element 132 and the third anchor element 142 in tension. In some embodiments, the multi-strand tethering element 120 may generally comprise two or more parallel strands, wires, and/or filaments, etc. fixedly secured and/or attached to the second anchor element 134 and the fourth anchor element 144.

A multi-strand linking element 150 may generally comprise two or more parallel strands, wires, and/or filaments, etc. configured to extend from the annuloplasty device 110 to the tethering element 120. In some embodiments, the multi-strand linking element 150 may generally comprise two or more parallel strands, wires, and/or filaments, etc. configured to extend between the annuloplasty device 110 and the tethering element 120 in tension. In some embodiments, the multi-strand linking element 150 connects to the tethering element 120 along a length of the tethering element 120. In some embodiments, the multi-strand linking element 150 may be slidable along the length of the tethering element 120. In some embodiments, the multi-strand linking element 150 is configured to be connected to the tethering element 120 at a location between the first portion of the tethering element 120 and the second portion of the tethering element 120. In some embodiments, the multi-strand linking element 150 is configured to be connected to the tethering element 120 at a location between the first papillary muscle 42 and the second papillary muscle 44. In some embodiments, the multi-strand linking element 150 is configured to be connected to the tethering element 120 at a location between the first anchor 130 and the second anchor 140, and/or between the second anchor element 134 and the fourth anchor element 144.

In some embodiments, the multi-strand linking element 150 extends through an anterior segment of the annuloplasty device 110. For example, each strand of the multi-strand linking element 150 may extend through the anterior segment of the annuloplasty device 110. In some embodiments, the multi-strand linking element 150 extends through the annuloplasty device 110 in a direction generally parallel to fluid flow through the mitral valve 18. In some embodiments, the multi-strand linking element 150 and/or each strand of the multi-strand linking element 150 is configured to extend through anterior tissue of the mitral valve 18 and/or the annulus of the mitral valve 18. For example, the annuloplasty device 110 and/or the multi-strand linking element 150 may be positioned and/or oriented relative to the mitral valve 18 such that the multi-strand linking element 150 and/or each strand of the multi-strand linking element 150 extends through the annuloplasty device 110 and anterior tissue of the mitral valve 18 (e.g., annulus, leaflet, etc.) at approximately a right angle to the coapting free edges of the valve leaflets.

In some embodiments, a first strand of the multi-strand linking element 150 may extend through the anterior segment of the annuloplasty device 110 and a second strand of the multi-strand linking element 150 may extend through a posterior segment of the annuloplasty device 110. In some embodiments, the first strand of the multi-strand linking element 150 is configured to extend through anterior tissue of the mitral valve 18, and the second strand of the multi-strand linking element 150 is configured to extend through posterior tissue of the mitral valve 18. For example, the annuloplasty device 110 and/or the multi-strand linking element 150 may be positioned and/or oriented relative to the mitral valve 18 such that the first strand of the multi-strand linking element 150 extends through the annuloplasty device 110 and anterior tissue of the mitral valve 18 (e.g., annulus, leaflet, etc.) at approximately a right angle to the coapting free edges of the valve leaflets and the second strand of the multi-strand linking element 150 extends through the annuloplasty device 110 and posterior tissue of the mitral valve 18 (e.g., annulus, leaflet, etc.) at approximately a right angle to the coapting free edges of the valve leaflets.

In at least some embodiments, the multi-strand linking element 150 may include a spring element 152 disposed between the annuloplasty device 110 and the tethering element 120. In some embodiments, each strand of the multi-strand linking element 150 may include a spring element 152 disposed between the annuloplasty device 110 and the tethering element 120. In some embodiments, each spring element 152 may be configured to maintain the multi-strand linking element 150 in tension between the annuloplasty device 110 and the tethering element 120. In some embodiments, each spring element 152 may maintain and/or assist in maintaining the tethering element 120 in tension between the first papillary muscle 42 and the second papillary muscle 44. In at least some embodiments, each spring element 152 may be formed from a resilient material and/or a shape memory material, for example nitinol or other suitable materials as described herein.

Figure 5:
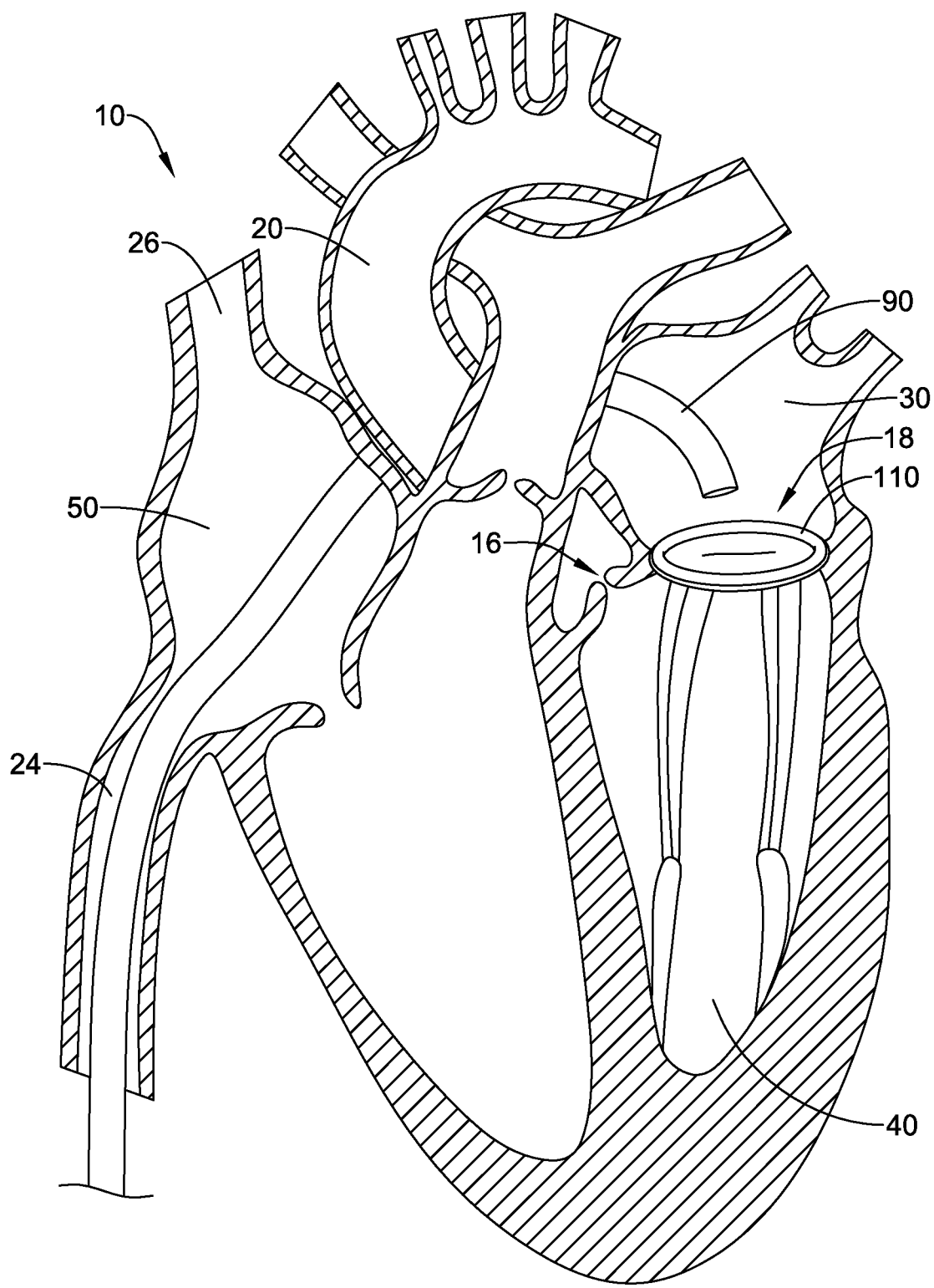
FIGS. 5-8 illustrate an example method of delivering the example mitral regurgitation treatment systems of the disclosure.

FIGS. 5-8 illustrate aspects of a method of delivering a mitral regurgitation treatment system 100. For example, the method may include inserting a delivery catheter 90 percutaneously through a vasculature to the left atrium 30 of the heart 10. In at least some embodiments, access to the left atrium 30 may be achieved using a transseptal approach, which may involve transiting the septum of the heart 10 between the left atrium 30 and the right atrium 50. The delivery catheter 90 may be advanced into right atrium 50 of the heart 10 through the inferior vena cava 24 or the superior vena cava 26 before transiting the septum and advancing into the left atrium 30. Alternative percutaneous approaches, through the aorta 20 and/or aortic valve 16 of the heart 10 into the left ventricle 40 for example, may also be used. Additional alternative delivery methods, including an apical approach via the apex of the left ventricle 40 of the heart 10 for example, are also contemplated. In some embodiments, the method may include deploying the annuloplasty device 110 from the delivery catheter 90 on the atrial side of the mitral valve 18 of the heart 10, as seen in FIG. 5. In some embodiments, the method may include positioning a distal end of the delivery catheter 90 adjacent an annuloplasty device 110 that was previously deployed on the atrial side of the mitral valve 18 of the heart 10. In this way, the tethering element 120 and/or the linking element 150 may be used with any suitable, existing annuloplasty device 110.

Figure 6:
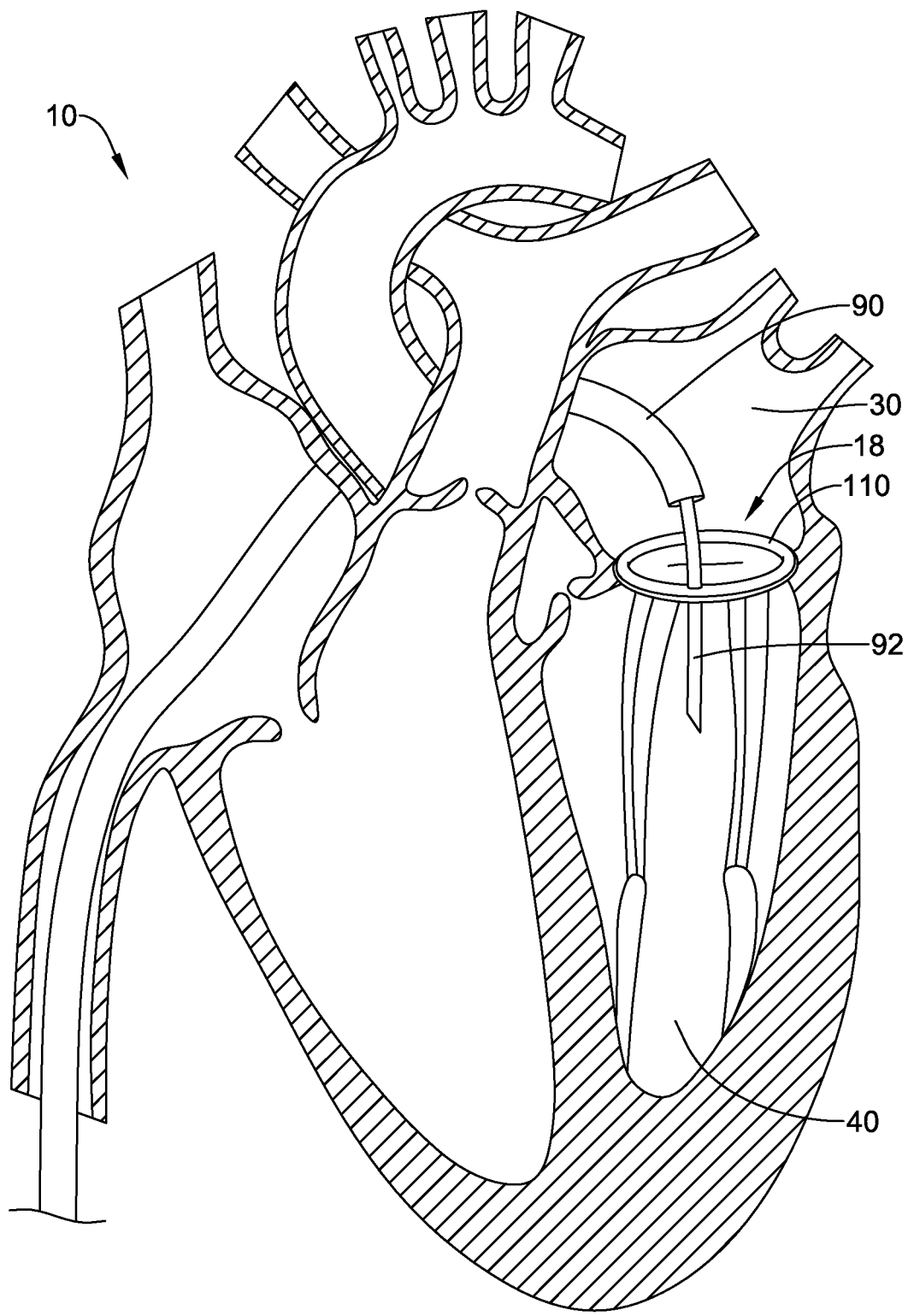

In some embodiments, the method may further include extending the tethering element 120 through the annuloplasty device 110 and into the left ventricle 40 of the heart 10. In at least some embodiments, extending the tethering element 120 through the annuloplasty device 110 includes extending an anchor delivery catheter 92 from the delivery catheter 90 through the annuloplasty device 110 and/or tissue of the mitral valve 18, and into the left ventricle 40 of the heart 10, as seen in FIG. 6 for example. In some embodiments, the anchor delivery catheter 92 may include a steerable piercing distal tip configured to pierce the annuloplasty device 110 and/or tissues of the heart 10. In some embodiments, the annuloplasty device 110 may include an aperture formed therein, the aperture being configured to permit the anchor delivery catheter 92, the tethering element 120, and/or the linking element 150 to pass therethrough.

Figure 7:
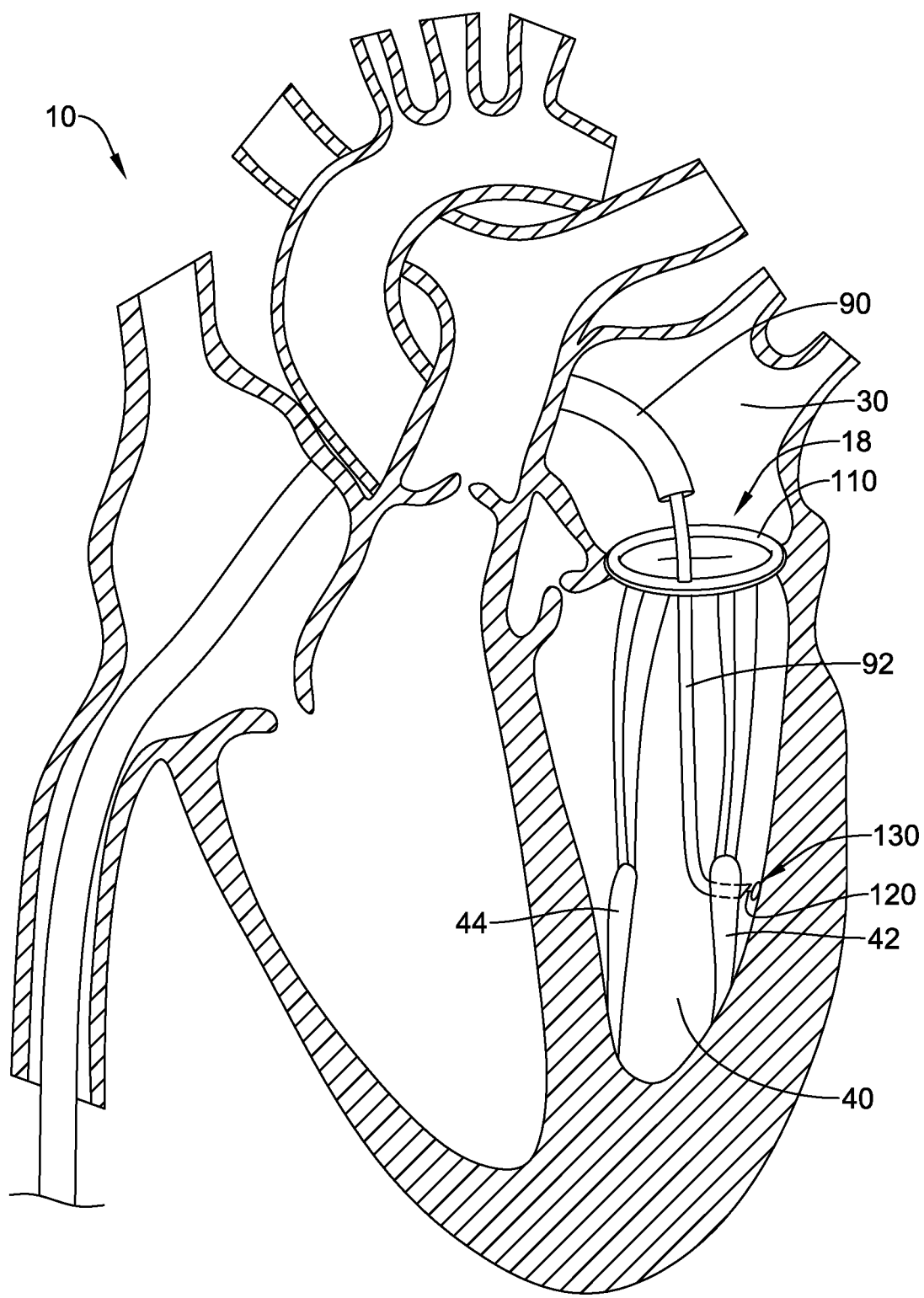
Figure 7A:
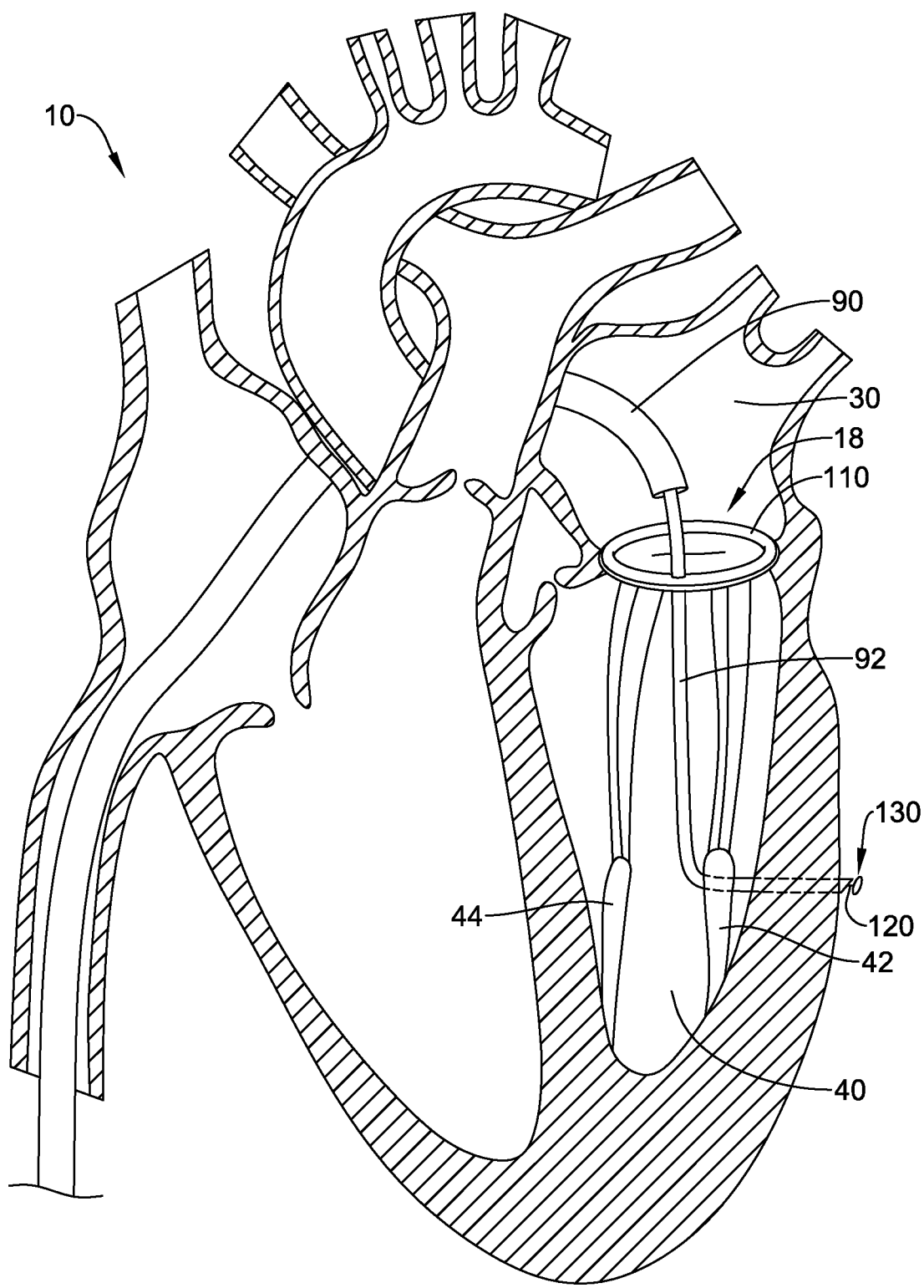

The method may include anchoring the tethering element 120 to the first papillary muscle 42, and anchoring the tethering element 120 to the second papillary muscle 44 such that the tethering element 120 is in tension between the first papillary muscle 42 and the second papillary muscle 44. In some embodiments, anchoring the tethering element 120 to the first papillary muscle 42 may include advancing the steerable piercing distal tip of the anchor delivery catheter 92 through the first papillary muscle 42, and subsequently advancing the first anchor 130 distally from the steerable piercing distal tip of the anchor delivery catheter 92, as seen in FIG. 7 for example. In some embodiments, the first anchor 130 may have its own piercing structure and/or feature, and the first anchor 130 may protrude distally from the anchor delivery catheter 92 before the first anchor 130 and/or the anchor delivery catheter 92 is advanced through the first papillary muscle 42. Anchoring the tethering element 120 to the first papillary muscle 42 may include passing the first portion of the tethering element 120 into and/or through the first papillary muscle 42. In some embodiments, a grasping structure may be used to locate, secure, and/or hold the first papillary muscle 42 prior to advancing the steerable piercing distal tip of the anchor delivery catheter 92 through the first papillary muscle 42. In an alternative method, anchoring the tethering element 120 to the first papillary muscle 42 may include advancing the steerable piercing distal tip of the anchor delivery catheter 92 through the first papillary muscle 42 and the wall of the left ventricle 40, and subsequently advancing the first anchor 130 distally from the steerable piercing distal tip of the anchor delivery catheter 92, as seen in FIG. 7A for example.

In some embodiments, anchoring the tethering element 120 to the second papillary muscle 44 may include advancing the steerable piercing distal tip of the anchor delivery catheter 92 through the second papillary muscle 44, and subsequently advancing the second anchor 140 distally from the steerable piercing distal tip of the anchor delivery catheter 92. In some embodiments, the second anchor 140 may have its own piercing structure and/or feature, and the second anchor 140 may protrude distally from the anchor delivery catheter 92 before the second anchor 140 and/or the anchor delivery catheter 92 is advanced through the second papillary muscle 44. Anchoring the tethering element 120 to the second papillary muscle 44 may include passing the second portion of the tethering element 120 into and/or through the second papillary muscle 44. In some embodiments, the grasping structure may be used to locate, secure, and/or hold the second papillary muscle 44 prior to advancing the steerable piercing distal tip of the anchor delivery catheter 92 through the second papillary muscle 44. In some embodiments, anchoring the tethering element 120 to the second papillary muscle 44 may include advancing the steerable piercing distal tip of the anchor delivery catheter 92 through the second papillary muscle 44 and the wall between the left ventricle 40 and the right ventricle 60, and subsequently advancing the second anchor 140 distally from the steerable piercing distal tip of the anchor delivery catheter 92.

In some embodiments, anchoring the tethering element 120 the first papillary muscle 42 may include advancing the steerable piercing distal tip of the anchor delivery catheter 92 through the first papillary muscle 42 and/or the wall of the left ventricle 40, and subsequently advancing the first anchor element 132 distally from the steerable piercing distal tip of the anchor delivery catheter 92. After withdrawing the steerable piercing distal tip of the anchor delivery catheter 92 from the first papillary muscle 42, the second anchor element 134 may be advanced distally from the steerable piercing distal tip of the anchor delivery catheter 92 and positioned against the outer surface of the first papillary muscle 42. In some embodiments, anchoring the tethering element 120 to the first papillary muscle 42 using the first anchor element 132 and the second anchor element 134 may spread tension and/or anchoring forces across a larger surface area and/or thickness of the first papillary muscle 42.

In some embodiments, anchoring the tethering element 120 to the second papillary muscle 44 may include advancing the steerable piercing distal tip of the anchor delivery catheter 92 through the second papillary muscle 44 and/or the wall between the left ventricle 40 and the right ventricle 60, and subsequently advancing the third anchor element 142 distally from the steerable piercing distal tip of the anchor delivery catheter 92. After withdrawing the steerable piercing distal tip of the anchor delivery catheter 92 from the second papillary muscle 44, the fourth anchor element 144 may be advanced distally from the steerable piercing distal tip of the anchor delivery catheter 92 and positioned against the outer surface of the second papillary muscle 44. In some embodiments, anchoring the tethering element 120 to the second papillary muscle 44 using the third anchor element 142 and the fourth anchor element 144 may spread tension and/or anchoring forces across a larger surface area and/or thickness of the second papillary muscle 44.

When anchoring the tethering element 120 to the first papillary muscle 42 and/or the second papillary muscle 44, the first papillary muscle 42 and/or the second papillary muscle 44 may be targeted using any suitable imaging method. For example, in some embodiments, the first papillary muscle 42 and/or the second papillary muscle 44 may be targeted using 3D ultrasound. Other suitable means of targeting the first papillary muscle 42 and/or the second papillary muscle 44 are also contemplated.

Figure 8:
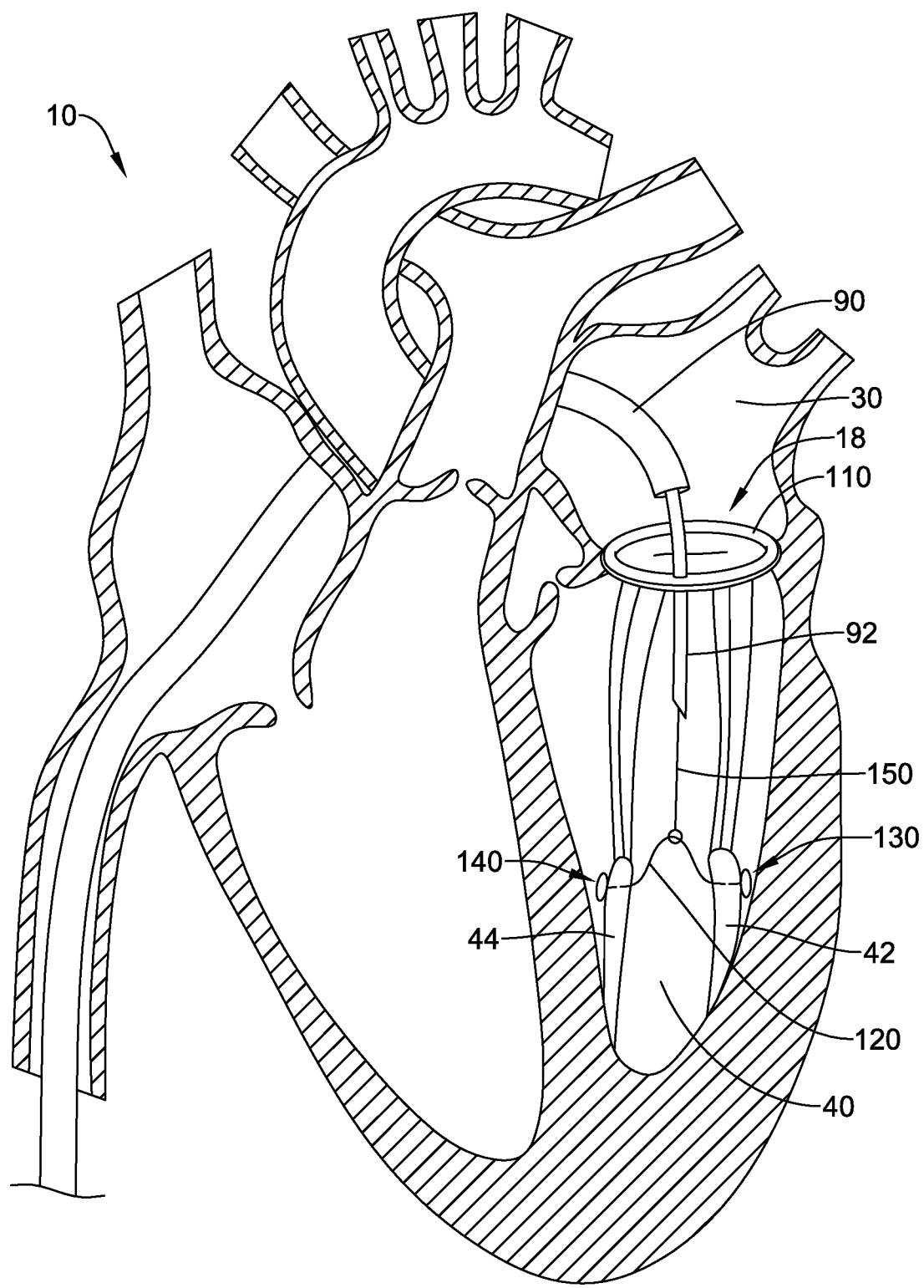

In some embodiments, the method may include securing the linking element 150 extending from the tethering element 120 to the annuloplasty device 110 in tension. The linking element 150 may include a spring element 152 disposed between the annuloplasty device 110 and the tethering element 120, and the linking element 150 may be slidably connected to the tethering element 120. After deploying the first anchor 130 and the second anchor 140, and/or after anchoring the tethering element 120 to the first papillary muscle 42 and the second papillary muscle 44, proximal withdrawal of the anchor delivery catheter 92 may release the linking element 150, as shown in FIG. 8 for example. Using one or more means known in the art, the linking element 150 may be held in tension as the anchor delivery catheter 92 is withdrawn. After the anchor delivery catheter 92 is withdrawn through the annuloplasty device 110, a crimping element 160 may be fed and/or advanced over the linking element 150 and into engagement with the outer surface of the annuloplasty device 110 (e.g., FIG. 3). With the linking element 150 held in tension, the crimping element 160 may be secured and/or fixedly attached to the linking element 150, thereby maintaining the linking element 150 in tension. Thereafter, the linking element 150 may be trimmed adjacent the crimping element 160, and the delivery catheter 90 and/or the anchor delivery catheter 92 may be withdrawn from the heart 10.

Figure 9:
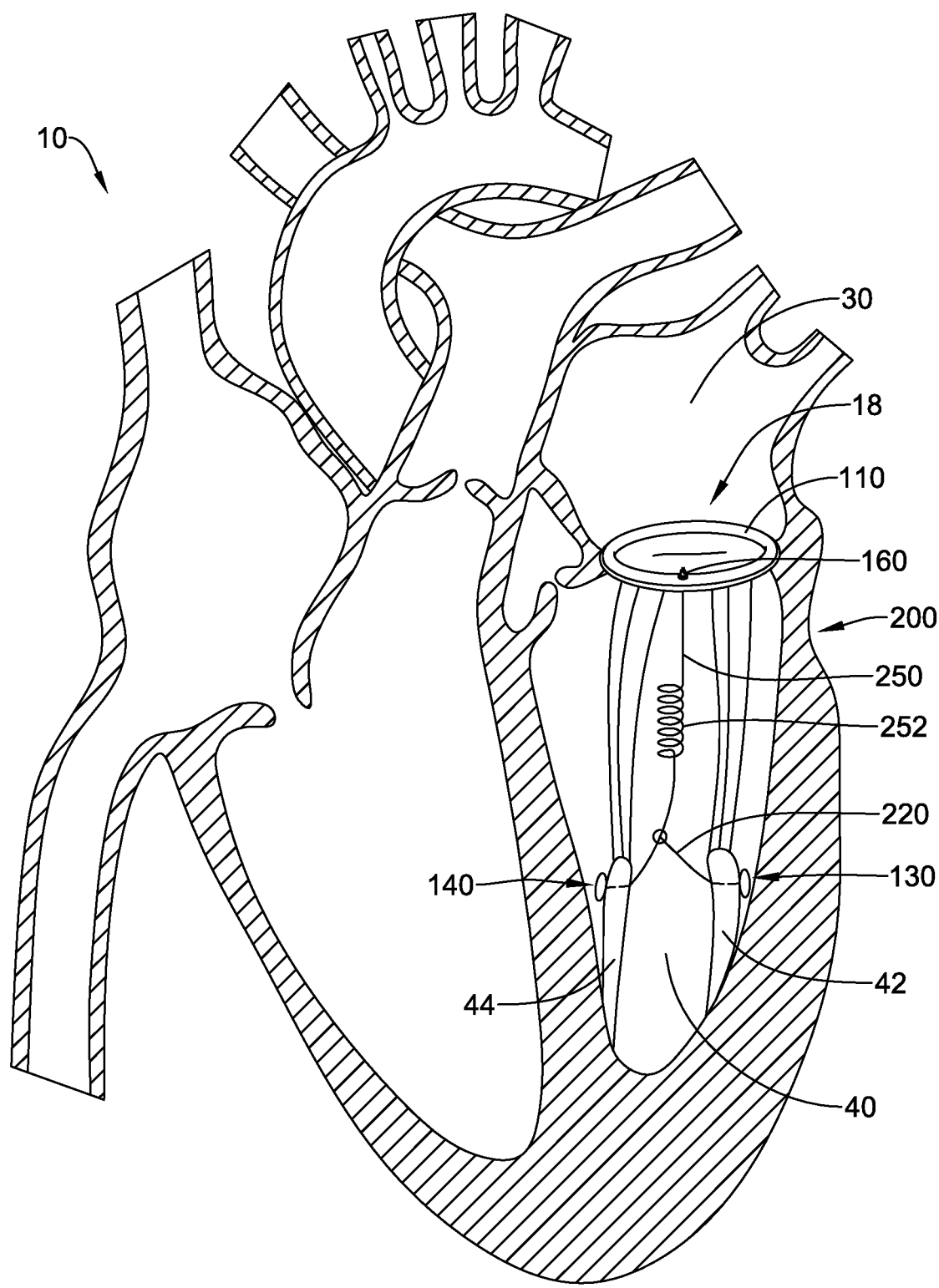
FIG. 9 illustrates an alternative configuration of a mitral regurgitation treatment system positioned relative to a mitral valve of the heart.

FIG. 9 illustrates an alternative configuration of a mitral regurgitation treatment system 200. The mitral regurgitation treatment system 200 may include the annuloplasty device 110 as described above. The mitral regurgitation treatment system 200 may include a linking element 250 extending from the annuloplasty device 110 to the first papillary muscle 42 or the second papillary muscle 44. The mitral regurgitation treatment system 200 may include a tethering element 220 extending from the linking element 250 to the other of the first papillary muscle 42 or the second papillary muscle 44. The linking element 250 may include a spring element 252 disposed between the annuloplasty device 110 and the tethering element 220. The mitral regurgitation treatment system 200 may include a first anchor 130 and a second anchor 140 configured to secure the linking element 250 and/or the tethering element 220 to the first papillary muscle 42 and/or the second papillary muscle 44. In the alternative configuration shown in FIG. 9, the linking element 250 may connect directly to one of the first papillary muscle 42 or the second papillary muscle 44, in contrast to the configuration(s) discussed above. In the alternative configuration of FIG. 9, the tethering element 220 does not extend between the first papillary muscle 42 and the second papillary muscle 44. Instead, the tethering element 220 connects one of the first papillary muscle 42 or the second papillary muscle 44 to the linking element 250. As such, when tension is applied to the linking element 250, the linking element 250 may slide through a loop at an end of the tethering element 220, thereby drawing the first papillary muscle 42 and the second papillary muscle 44 closer together while also pulling the first papillary muscle 42 and/or the second papillary muscle toward the annuloplasty device 110 and/or the mitral valve 18 to relieve tension and/or directional vectoring on the chordae and improve leaflet coaptation. Similar to the configurations described above, the linking element 250 and/or the tethering element 220 may include multi-strand configurations. Other elements, methods of use, and/or features not specifically discussed with respect to FIG. 9 (e.g., the crimping element 160, the anchoring elements 130/140, etc.) may be substantially the same as described with respect to other embodiments and/or configurations herein.

Figure 10A:
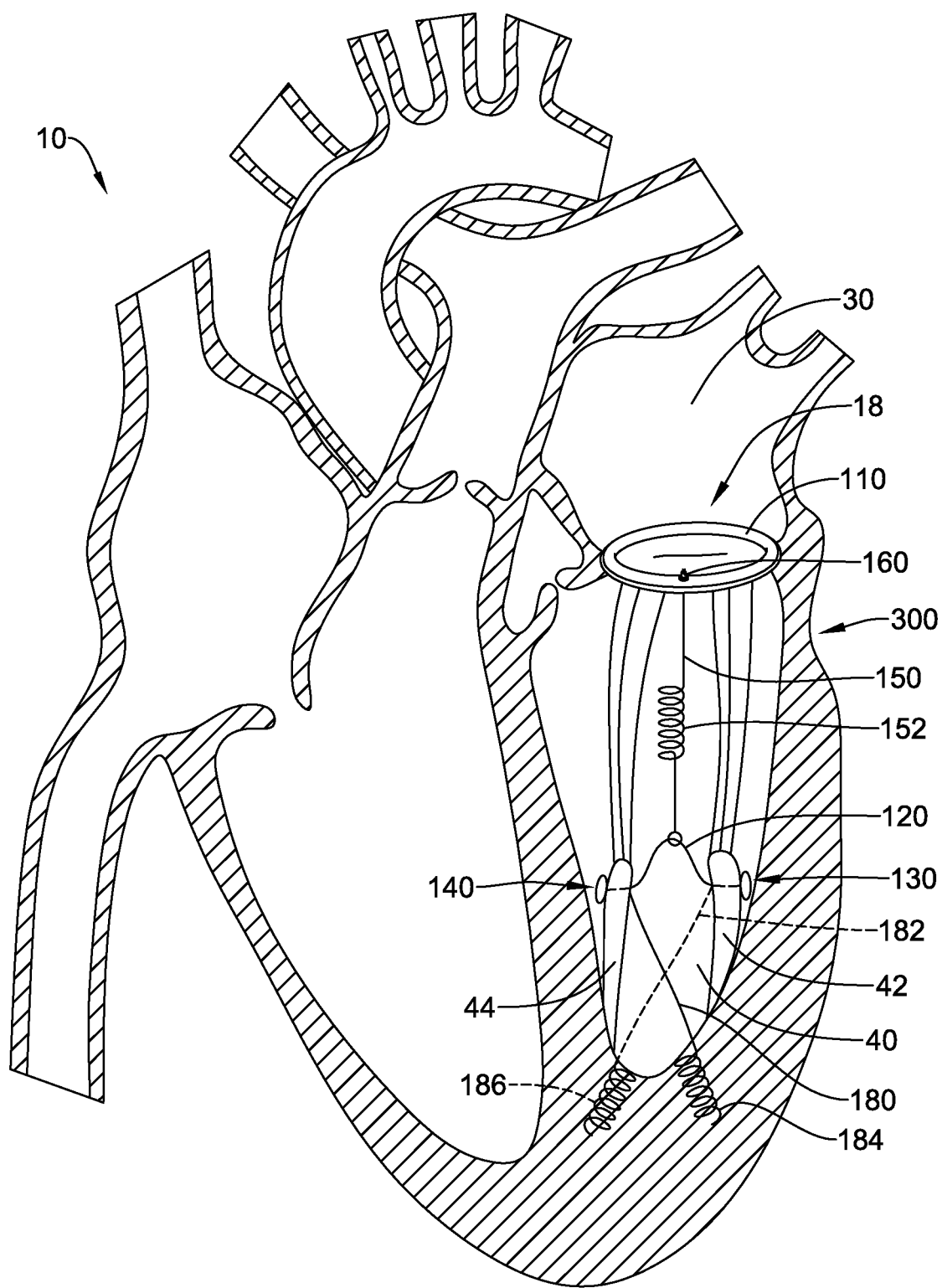
FIGS. 10A and 10B illustrate alternative configurations of a mitral regurgitation treatment system positioned relative to a mitral valve of the heart.

FIG. 10A illustrates alternative configurations of a mitral regurgitation treatment system 300. The mitral regurgitation treatment system 300 may include similar features to and/or may be substantially the same as the mitral regurgitation treatment system 100 described above. Additionally, the mitral regurgitation treatment system 300 may further include a second tethering element 180 and/or a third tethering element 182 (shown in phantom). The second tethering element 180 may be secured and/or attached to the second anchor 140 and/or the tethering element 120 at a first end. The second tethering element 180 may include an attachment element 184 at a second end opposite the first end, wherein the attachment element 184 is configured to anchor the second tethering element 180 to the wall of the left ventricle 40, thereby adding and/or applying an additional force vector to the second papillary muscle 44 and/or the tethering element 120, and consequently to the linking element 150, for repositioning the second papillary muscle 44 and/or altering tension and/or directional vectors on the chordae and the valve leaflets connected thereto. The third tethering element 182 may be secured and/or attached to the first anchor 130 and/or the tethering element 120 at a first end. The third tethering element 182 may include an attachment element 186 at a second end opposite the first end, wherein the attachment element 186 is configured to anchor the third tethering element 182 to the wall of the left ventricle 40, thereby adding and/or applying an additional force vector to the first papillary muscle 42 and/or the tethering element 120, and consequently to the linking element 150, for repositioning the first papillary muscle 42 and/or altering tension and/or directional vectors on the chordae and the valve leaflets connected thereto. In some embodiments, the attachment element 184/186 may be a screw-type anchor, a coiled anchor, a rivet, a barbed spike, etc. capable of attaching the second tethering element 180 and/or the third tethering element 182 to the wall of the left ventricle 40.

Figure 10B:
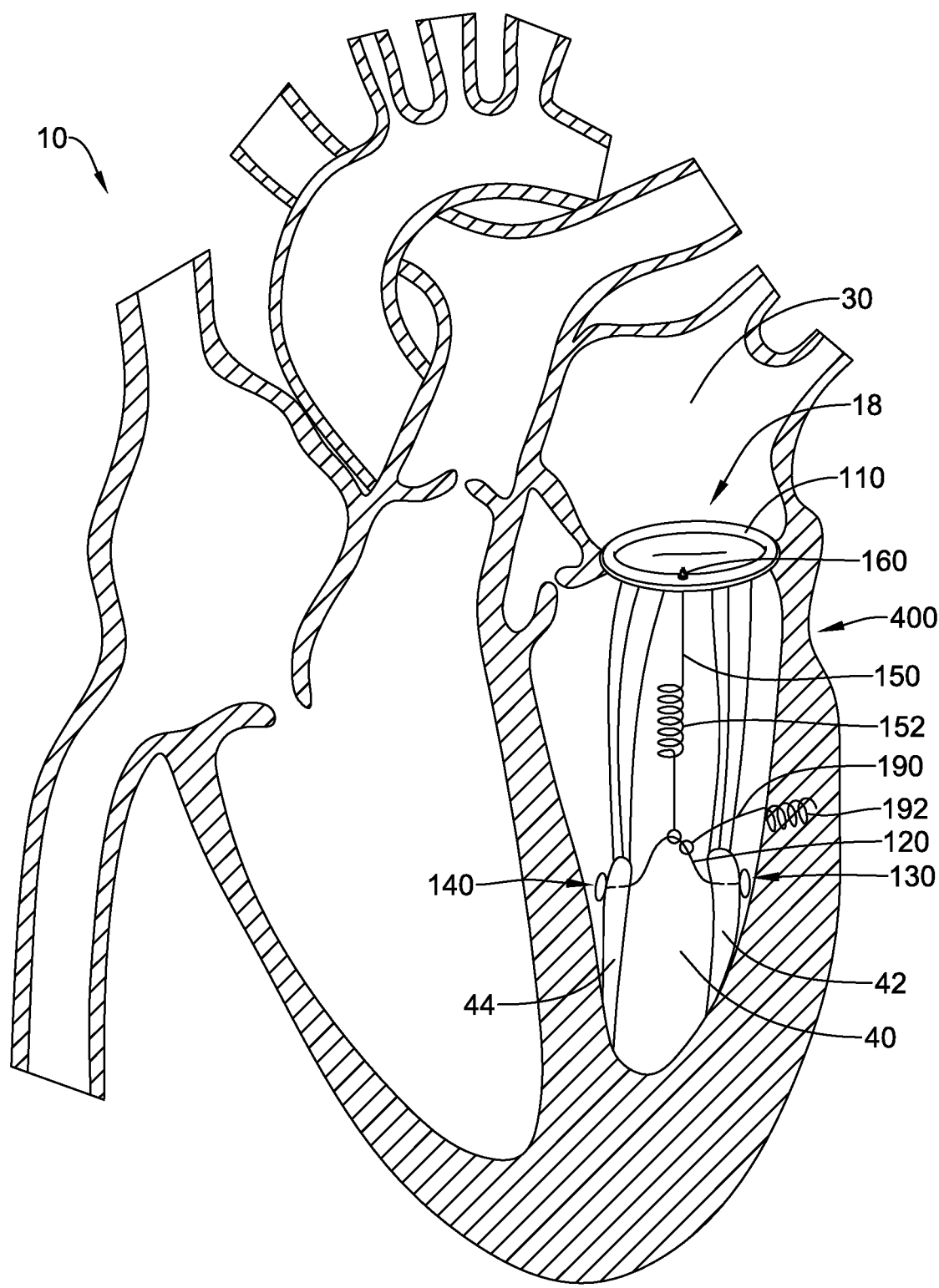

As an alternative to the configuration of FIG. 10A, a mitral regurgitation treatment system 400, shown in FIG. 10B and which may include similar features to and/or may be substantially the same as the mitral regurgitation treatment system 300 described above, may include a fourth tethering element 190 instead of, or in addition to, the second tethering element 180 and/or the third tethering element 182. A first end of the fourth tethering element 190 may be secured and/or attached to the tethering element 120 along the length of the tethering element 120 between the first papillary muscle 42 and the second papillary muscle 44, between the first portion of the tethering element 120 and the second portion of the tethering element 120, etc. In some embodiments, the first end of the fourth tethering element 190 may be secured and/or attached to the tethering element 120 as the same location as the linking element 150. The fourth tethering element 190 may include an attachment element 192 at a second end opposite the first end, wherein the attachment element 192 is configured to anchor the fourth tethering element 190 to the wall of the left ventricle 40, thereby adding and/or applying an additional force vector to the first papillary muscle 42, the second papillary muscle 44, and/or the tethering element 120, and consequently to the linking element 150, for repositioning the first papillary muscle 42 and/or the second papillary muscle 44, and/or altering tension and/or directional vectors on the chordae and the valve leaflets connected thereto. In some embodiments, the attachment element 192 may be a screw-type anchor, a coiled anchor, a rivet, a barbed spike, etc. capable of attaching the fourth tethering element 190 to the wall of the left ventricle 40.

The materials that can be used for the various components of the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. (and/or other systems or components disclosed herein) and the various elements thereof disclosed herein may include those commonly associated with medical devices. For simplicity purposes, the following discussion makes reference to the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. However, this is not intended to limit the devices and methods described herein, as the discussion may be applied to other elements, members, components, or devices disclosed herein, such as, but not limited to, the first anchor element 132, the second anchor element 134, the third anchor element 142, the fourth anchor element 144, the spring element 152, the spring element 252, etc. and/or elements or components thereof.

In some embodiments, the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. to achieve the same result.

In some embodiments, a degree of Magnetic Resonance Imaging (MRI) compatibility is imparted into the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. For example, the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc., and/or components or portions thereof, may be made of a material that does not substantially distort the image and create substantial artifacts (e.g., gaps in the image). Certain ferromagnetic materials, for example, may not be suitable because they may create artifacts in an MM image. The delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc., or portions thereof, may also be made from a material that the MM machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyl s, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the delivery catheter 90, the anchor delivery catheter 92, the mitral regurgitation treatment system 100, the annuloplasty device 110, the tethering element 120, the first anchor 130, the second anchor 140, the linking element 150, the crimping element 160, the second tethering element 180, the third tethering element 182, the fourth tethering element 190, the mitral regurgitation treatment system 200, the tethering element 220, the linking element 250, the mitral regurgitation treatment system 300, and/or the mitral regurgitation treatment system 400, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A mitral regurgitation treatment system, comprising:
an annuloplasty device configured for placement on an atrial side of a mitral valve;
a tethering element configured to extend between a first papillary muscle and a second papillary muscle, wherein the tethering element includes a first anchor securing the tethering element to the first papillary muscle and a second anchor securing the tethering element to the second papillary muscle; and
a linking element extending from the annuloplasty device to the tethering element;
wherein the linking element includes a spring element disposed between the annuloplasty device and the tethering element;

wherein the first anchor includes a first anchoring element configured to be positioned against an outer surface of the first papillary muscle and a second anchoring element configured to be positioned against the outer surface of the first papillary muscle opposite the first anchoring element such that the first papillary muscle is disposed between the first anchoring element and the second anchoring element and a first portion of the tethering element passes through the first papillary muscle;

wherein the second anchor includes a third anchoring element configured to be positioned against an outer surface of the second papillary muscle and a fourth anchoring element configured to be positioned against the outer surface of the second papillary muscle opposite the third anchoring element such that the second papillary muscle is disposed between the third anchoring element and the fourth anchoring element and a second portion of the tethering element passes through the second papillary muscle.

2. The mitral regurgitation treatment system of claim 1, wherein the linking element connects to the tethering element along a length of the tethering element.

3. The mitral regurgitation treatment system of claim 1, wherein the linking element is configured to connect to the tethering element at a location between the first papillary muscle and the second papillary muscle.

4. The mitral regurgitation treatment system of claim 1, wherein the spring element maintains the linking element in tension between the annuloplasty device and the tethering element.

5. The mitral regurgitation treatment system of claim 4, further comprising a crimping element disposed on the linking element and configured to engage an outer surface of the annuloplasty device.

6. The mitral regurgitation treatment system of claim 1, wherein the linking element extends through the annuloplasty device.

7. The mitral regurgitation treatment system of claim 6, wherein the linking element extends through the annuloplasty device in a direction generally parallel to fluid flow through the mitral valve.

8. The mitral regurgitation treatment system of claim 1, wherein the linking element is configured to extend through tissue of the mitral valve.

9. The mitral regurgitation treatment system of claim 1, wherein the spring element is formed from nitinol.

10. A mitral regurgitation treatment system, comprising:
an annuloplasty device configured for placement on an atrial side of a mitral valve;
a tethering element configured to extend between a first papillary muscle and a second papillary muscle, wherein the tethering element includes a first anchor securing the tethering element to the first papillary muscle and a second anchor securing the tethering element to the second papillary muscle; and
a linking element extending from the annuloplasty device to the tethering element;
wherein the first anchor includes a first anchoring element configured to be positioned against an outer surface of the first papillary muscle and a second anchoring element configured to be positioned against the outer surface of the first papillary muscle opposite the first anchoring element such that the first papillary muscle is disposed between the first anchoring element and the second anchoring element and a first portion of the tethering element passes through the first papillary muscle;

wherein the second anchor includes a third anchoring element configured to be positioned against an outer surface of the second papillary muscle and a fourth anchoring element configured to be positioned against the outer surface of the second papillary muscle opposite the third anchoring element such that the second papillary muscle is disposed between the third anchoring element and the fourth anchoring element and a second portion of the tethering element passes through the second papillary muscle.

11. The mitral regurgitation treatment system of claim 10, wherein the linking element is connected to the tethering element between the first portion and the second portion.

12. The mitral regurgitation treatment system of claim 11, wherein the linking element is slidable along the tethering element.

13. The mitral regurgitation treatment system of claim 10, wherein at least one of the tethering element and the linking element comprise a multi-strand suture.

14. The mitral regurgitation treatment system of claim 10, wherein the tethering element is configured to extend between the first papillary muscle and the second papillary muscle in tension.

15. A method of delivering a mitral regurgitation system, comprising:
inserting a delivery catheter percutaneously through a vasculature to a left atrium of a heart;
deploying an annuloplasty device from the delivery catheter on an atrial side of a mitral valve of the heart;
extending a tethering element through the annuloplasty device and into a left ventricle of the heart;
anchoring the tethering element to a first papillary muscle;
anchoring the tethering element to a second papillary muscle such that the tethering element is in tension between the first papillary muscle and the second papillary muscle; and
securing a linking element extending from the tethering element to the annuloplasty device in tension, the linking element including a spring element disposed between the annuloplasty device and the tethering element.

16. The method of claim 15, wherein extending the tethering element includes extending an anchor delivery catheter from the delivery catheter through the annuloplasty device and into the left ventricle of the heart.

17. The method of claim 15, wherein anchoring the tethering element to the first papillary muscle includes passing a first portion of the tethering element through the first papillary muscle.

18. The method of claim 15, wherein anchoring the tethering element to the second papillary muscle includes passing a second portion of the tethering element through the second papillary muscle.

19. The method of claim 15, wherein securing the linking element includes feeding a crimping element over the linking element and into engagement with the annuloplasty device.

\* \* \* \* \*